US012721568B2

(12) United States Patent
Sherman

(10) Patent No.: US 12,721,568 B2
(45) Date of Patent: Sep. 1, 2026

(54) SLEEP AGE DETERMINATION FROM WEARABLE-BASED PHYSIOLOGICAL DATA

(71) Applicant: Oura Health Oy, Oulu (FI)

(72) Inventor: Jake Harris Sherman, Seattle, WA (US)

(73) Assignee: Oura Health Oy, Oulu (FI)

( * ) Notice: Subject to any disclaimer, the term of this patent is extended or adjusted under 35 U.S.C. 154(b) by 174 days.

(21) Appl. No.: 18/455,514

(22) Filed: Aug. 24, 2023

(65) Prior Publication Data

US 2025/0064387 A1 Feb. 27, 2025

(51) Int. Cl.
*A61B 5/00* (2006.01)
*A61B 5/024* (2006.01)

(52) U.S. Cl.
CPC ........ *A61B 5/4812* (2013.01); *A61B 5/02416* (2013.01); *A61B 5/6802* (2013.01); *A61B 5/7267* (2013.01); *A61B 5/7271* (2013.01); *A61B 5/7435* (2013.01)

(58) Field of Classification Search
CPC . A61B 5/4812; A61B 5/02416; A61B 5/6802; A61B 5/7267; A61B 5/7271; A61B 5/7435; A61B 5/02438; A61B 5/02405; A61B 5/02055; A61B 5/7275
See application file for complete search history.

(56) References Cited

U.S. PATENT DOCUMENTS

2016/0270718 A1* 9/2016 Heneghan .............. G16H 50/30
2021/0401378 A1* 12/2021 Pho ...................... A61B 5/0008

FOREIGN PATENT DOCUMENTS

WO WO-2018023135 A1 * 2/2018 ........... A61B 5/0036

* cited by examiner

*Primary Examiner* — Sana Sahand
(74) *Attorney, Agent, or Firm* — ArentFox Schiff LLP

(57) ABSTRACT

Methods, systems, and devices for determining a sleep age metric of a user are described. The system may receive photoplethysmogram (PPG) data throughout a time interval including a plurality of sleep intervals during which the user is asleep, input the PPG data into a first machine learning model, and classify the PPG data into a plurality of sleep stages. The system may input one or more sleep features into a second machine learning model, and the second machine learning model may output a sleep age metric associated with a sleep health of the user relative to a chronological age of the user. In some cases, the system may transmit, to a user device, an instruction to cause a graphical user interface (GUI) to display an indication of the sleep age metric and an insight for a value of the sleep age metric.

19 Claims, 12 Drawing Sheets

SLEEP AGE DETERMINATION FROM WEARABLE-BASED PHYSIOLOGICAL DATA

FIELD OF TECHNOLOGY

The following relates to wearable devices and data processing, including sleep age determination from wearable-based physiological data.

BACKGROUND

Some wearable devices may be configured to collect data from users including photoplethysmogram (PPG) data, heart rate data, and the like. For example, some wearable devices may be configured to collect physiological data associated with the sleep health of a user.

DETAILED DESCRIPTION

Figure 1:
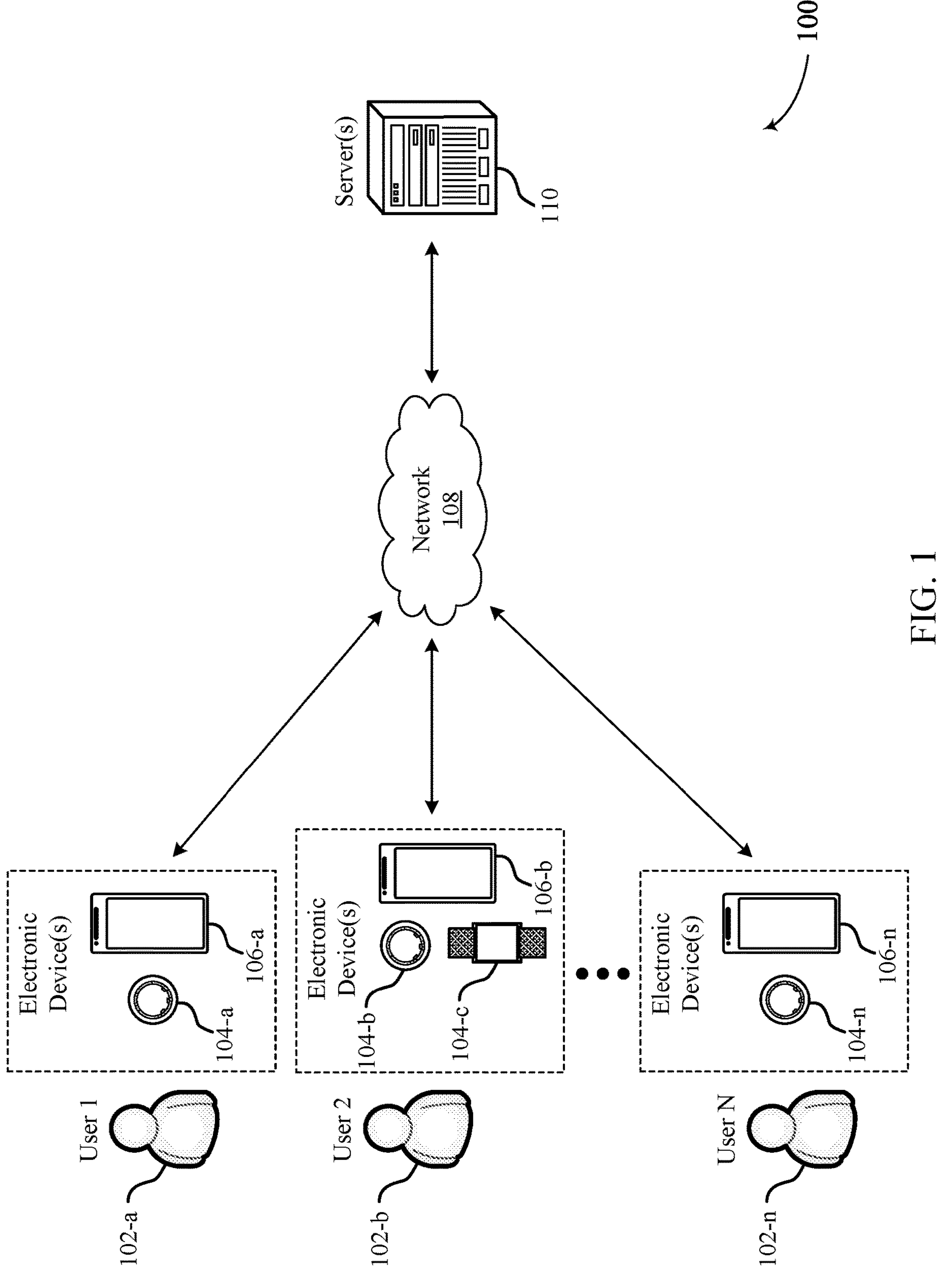
FIG. 1 illustrates an example of a system that supports sleep age determination from wearable-based physiological data in accordance with aspects of the present disclosure.

Some wearable devices may be configured to collect physiological data from users, including photoplethysmogram (PPG) data, temperature data, heart rate, heart rate variability (HRV) data, sleep data, respiratory data, blood pressure data, and the like. Acquired physiological data may be used to analyze behavioral and physiological characteristics associated with the user, such as movement, and the like. Many users have a desire for more insight regarding their physical health, including their activity patterns, sleep patterns, and overall physical well-being. In particular, many users may have a desire for more insight regarding their sleep health, including a sleep age that correlates to a user's overall health based on the quality of their sleep. However, typical techniques to measure sleep health and health devices and/or applications lack the ability to provide robust determination and insight for several reasons.

For example, other health devices and applications (e.g., lab-based sleep studies) may obtain sleep data from a single night of sleep, and the sleep health metrics may be calculated based on data (e.g., polysomnography (PSG) or electroencephalography (EEG) signals) received during the sleep study. As such, because sleep studies are usually based on data collected over a single night, such sleep studies may illustrate only a small snapshot of the user's long term sleeping health. Even for devices that are wearable or that collect a user's physiological data, typical devices and applications lack the ability to collect other physiological, behavioral, or contextual inputs from the user that can be combined with the measured data to more comprehensively understand the complete set of physiological contributors to a user's sleep health.

Further, some sleep studies calculate sleep health metrics by inputting raw signals (e.g., raw PSG and/or EEG data) into machine learning models. As such, because the sleep health metrics are calculated based on raw signals, such sleep studies may be unable to answer "why" the user's sleep health metrics are calculated the way they were. Therefore, while such sleep studies may provide accurate sleep health metrics, they may not be able to provide the user with actionable insights to help the user improve the sleep health metrics.

Aspects of the present disclosure are directed to techniques for determining a sleep age metric from wearable-based physiological data. For the purposes of the present disclosure, the term "sleep age metric," "sleep health metric," "sleep age," and like terms, may be used to refer to a sleep health metric of the user relative to their chronological age. Sleep age (e.g., brain age and/or brain health) is a metric used to understand the user's overall health and provide an assessment of aging based on a user's sleep health. A sleep age of the user may provide an assessment of the user's aging based on the user's sleep health. Specifically, a difference between a user's calculated sleep age and their actual chronological age may be predictive of many health conditions.

Sleep age is a long-term metric that is calculated using weeks and/or months of data, and may provide a longer-term view into a user's sleep health (and overall health). As compared to sleep studies which may calculate a user's sleep age using raw PSG and/or EEG signals, aspects of the present disclosure are directed to techniques for calculating a user's sleep age based on features extracted from a sleep staging algorithm, such as percent of time in different sleep stages, a fragmentation of the user's sleep, a midpoint of the user's sleep, and the like.

In particular, computing devices of the present disclosure may receive physiological data from the wearable device associated with the user. The physiological data may include at least PPG data for the user. Aspects of the present disclosure may input, using one or more processors communicatively coupled with the wearable device, the PPG data into a first machine learning model. In some examples, aspects of the present disclosure may classify, as part of a sleep staging classification procedure and using the first machine learning model, the PPG data collected during the plurality of sleep intervals into a plurality of sleep stages. The plurality of sleep stages may include at least an awake sleep stage, a light sleep stage, a deep sleep stage, a rapid eye movement (REM) sleep stage, or any combination thereof.

In some cases, computing devices of the present disclosure may input one or more sleep features from the sleep staging classification procedure into a second machine learning model based on classifying the PPG data. The one or more sleep features may include at least a duration that the user spent in each of the plurality of sleep stages. Aspects of the present disclosure may output, from the second machine learning model, the sleep age metric. As such, aspects of the present disclosure may provide techniques for determining the sleep age metric for the user based on inputting the one or more sleep features into the second machine learning model, where the sleep age metric indicates a sleep health of the user relative to a chronological age of the user.

The second machine learning model may be trained to determine sleep ages based on outputs of the sleep staging algorithm (e.g., sleep features) in addition to the sleep staging inputs (e.g., a transformed PPG signal). By estimating a user's sleep age based on sleep staging features (e.g., percent of time in different sleep stages, and the like), rather than raw PSG and/or EEG signals, the system may be able to determine why the user's sleep age was calculated the way it was, and may therefore be able to provide actionable recommendations of how to improve the user's sleep age. For example, the system may determine that the user's sleep age is higher than their chronological age due to the user achieving relatively low deep sleep. In this example, the system may leverage previous data collected by the user to determine that the user achieves more deep sleep when they go for a walk before bed, and may therefore suggest that the user take walks before their bedtime to increase their deep sleep, and thereby improve their sleep age metric. As such, techniques for determining the sleep age may provide the user with a new measure of sleep quality, along with more actionable insights to improve the user's overall health.

In some cases, determining a sleep age metric may enable the system described herein to provide actionable guidance to improve the user's sleep age, which may reduce later-life health risks for users. In such cases, techniques to determine the sleep age metric and provide recommendations for improving the sleep age metric for users may be desired in order to improve quality of life, sleep, and mood, and to reduce future health risks. For example, methods and techniques to help users understand in a personalized way how to optimize lifestyle changes to improve their sleep age metric or maintain their sleep age metric may be desired. The system may be able to determine a sleep age metric relative to the chronological age of the user in order to provide metrics that may enable users to understand how behavior changes (e.g., improvements in sleep, exercise, diet, and mood) may help improve their sleep age metric and reduce the risks for disease, and the like.

Techniques described herein may notify a user of the determined sleep age metric in a variety of ways. For example, a system may cause a graphical user interface (GUI) of a user device to display a message or other notification to notify the user of the determined sleep age metric and make recommendations to the user. In one example, the system may display the user's sleep age along with an explanation or rationale as to why the user's sleep age was calculated to be what it is. For example, the explanation or rationale may indicate that "Your percent of deep sleep is lower than normal, which is contributing to your poor sleep age. Try taking cold showers before bed to increase your deep sleep and thereby improve your sleep age." A GUI may also include graphics/text which indicate the data used to make the sleep age metric.

Aspects of the disclosure are initially described in the context of systems supporting physiological data collection from users via wearable devices. Additional aspects of the disclosure are described in the context of example data diagrams and an example GUI. Aspects of the disclosure are further illustrated by and described with reference to apparatus diagrams, system diagrams, and flowcharts that relate to sleep age determination from wearable-based physiological data.

FIG. 1 illustrates an example of a system 100 that supports sleep age determination from wearable-based physiological data in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-c (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a REM sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for determining a sleep age metric of a user 102 from wearable-based physiological data. In particular, the system 100 illustrated in FIG. 1 may support techniques for determining a sleep age metric that indicates a sleep health of the user 102 relative to a chronological age of the user 102, and causes a user device 106 corresponding to the user 102 to display the indication of the sleep metric. The indication of the sleep age metric may be based on at least received PPG data measured from the user 102 by a wearable device 104 throughout a time interval including a plurality of sleep intervals during which the user 102 is asleep. The indication of the sleep age metric may also be based on one or more sleep features from a sleep staging classification procedure. The one or more sleep features may include at least a duration that the user 102 spent in each of the plurality of sleep stages. As part of a sleep staging classification procedure, the PPG data collected during the plurality of sleep intervals may be classified into a plurality of sleep stages including an awake sleep stage, a light sleep stage, a deep sleep stage, a REM sleep stage, or any combination thereof.

For example, as shown in FIG. 1, User 1 (user 102-*a*) may be associated with a wearable device 104-*a* (e.g., ring 104-*a*) and a user device 106-*a*. In this example, the ring 104-*a* may collect data associated with the user 102-*a*, including the PPG signal, temperature, heart rate, HRV, respiratory rate, and the like. In some aspects, data collected by the ring 104-*a* may be used to determine the sleep age metric of the user 102 relative to the chronological age of the user 102. Determining the sleep age metric may be performed by any of the components of the system 100, including the ring 104-*a*, the user device 106-*a* associated with User 1, the one or more servers 110, or any combination thereof. Upon determining the sleep age metric, the system 100 may selectively cause the GUI of the user device 106 to display the indication of the sleep age metric and/or an insight for a value of the sleep age metric. The system 100 may transmit, to the user device 106 associated with the wearable device 104, an instruction to cause the GUI of the user device 106 to display the indication of the sleep age metric and the insight for a value of the sleep age metric.

In some implementations, upon receiving physiological data (e.g., including the PPG signal), the system 100 may input the PPG data into a first machine learning model. In such cases, the system 100 may use the first machine learning model to classify the PPG data into the plurality of sleep stages. The system 100 may input the one or more sleep features into a second machine learning model. The second machine learning model may output the sleep age metric in response to inputting the sleep features.

In some implementations, the system 100 may generate alerts, messages, or recommendations for User 1, User, 2, and/or User N (e.g., via the ring 104-*a*, user device 106-*a*, or both) based on the determined sleep age metric, where the messages may provide insights for a value of the sleep age metric, and the like. For example, the system 100 may display insights as to why the user's sleep age metric differs from their chronological age. In some cases, the messages may provide educational videos and/or text (e.g., content) associated with the sleep age metric, recommendations to improve the sleep age metric, explanations as to why the user's sleep age metric is below (e.g., younger) or above (e.g., older) than their chronological age, explanation as to how the user has successfully improved their sleep age metric, an adjusted set of activity and/or sleep targets, or a combination thereof.

The difference between a user's sleep age and chronological age may serve as a longer-term health metric compared to Sleep Scores and allow users to observe over time how their actual age tracks with their sleep age. As described herein, sleep age provides an assessment of aging based on a user's sleep habits, such as time spent in sleep stages, sleep fragmentation (e.g., how often the user wakes up during the night), sleep latency (e.g., how long it takes the user to fall asleep), sleep midpoint, and the like. Additionally, the system may provide users with insight into how long-term behavior affects the difference between sleep age and actual chronological age and offer personalized recommendations for improving sleep age.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
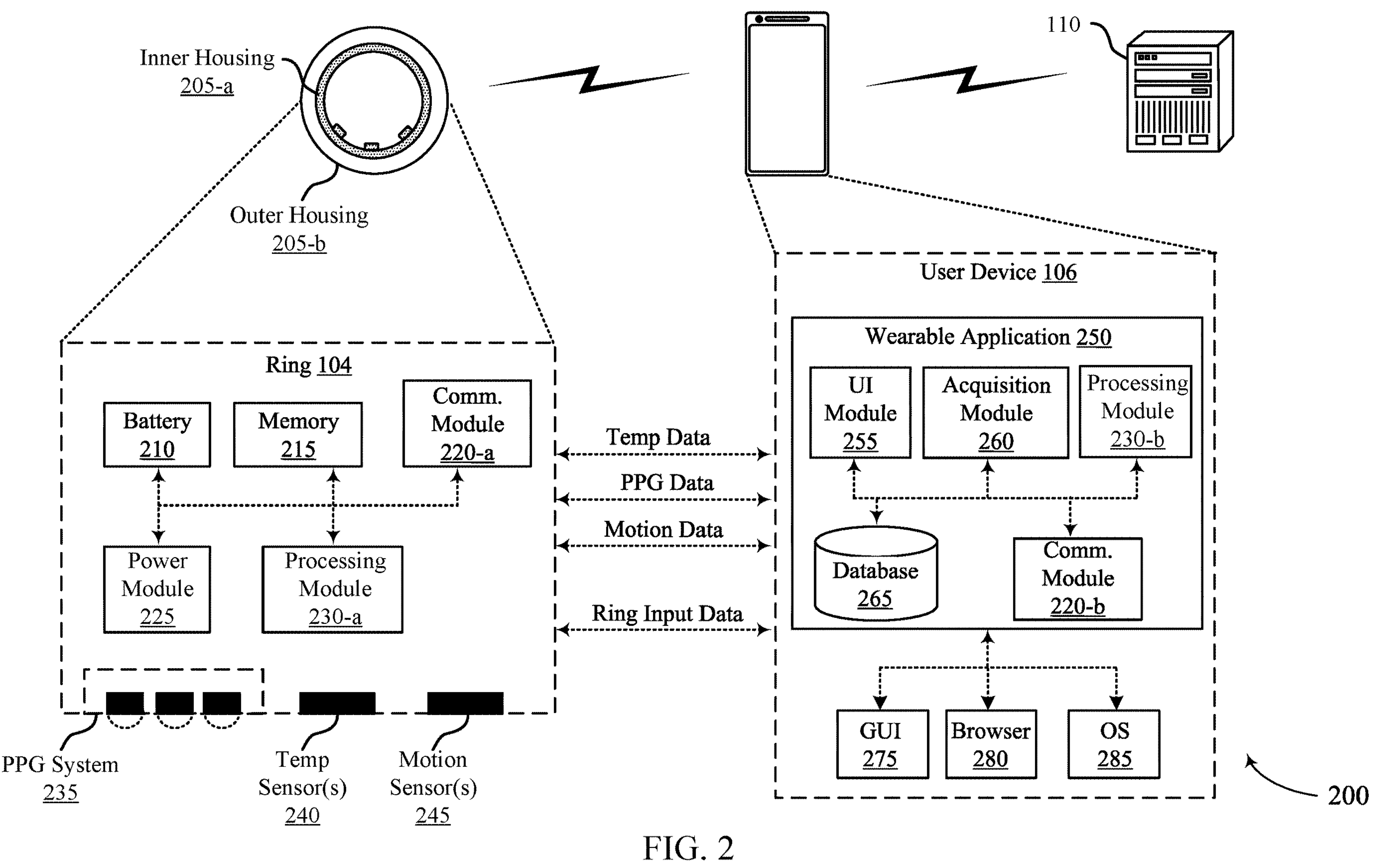
FIG. 2 illustrates an example of a system that supports sleep age determination from wearable-based physiological data in accordance with aspects of the present disclosure.

FIG. 2 illustrates an example of a system 200 that supports sleep age determination from wearable-based physiological data in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers.

As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep day's may be offset relative to calendar days. For example, sleep day's may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for determining a sleep age metric of a user from wearable-based physiological data. In particular, the respective components of the system 200 may be used to determine a sleep age metric that indicates a sleep health of the user relative to a chronological age of the user based on classifying received PPG data into a plurality of sleep stages and inputting one or more sleep features from the plurality of sleep stages into a machine learning model. The indication of the sleep age metric for the user may be determined by leveraging PPG sensors on the ring 104 of the system 200.

For example, as noted previously herein, the ring 104 of the system 200 may be worn by a user to collect data from the user, including the PPG signal, temperature, heart rate, HRV, respiratory data, sleep data, and the like. The ring 104 of the system 200 may collect the physiological data from the user based on PPG sensors and measurements extracted from arterial blood flow (e.g., using PPG signals), capillary blood flow; arteriole blood flow, or a combination thereof. The physiological data may be collected continuously. In some implementations, the processing module 230-*a* may sample and/or receive the user's PPG signal continuously throughout the day and night. Sampling at a sufficient rate (e.g., one sample per second or one sample per minute) throughout the day and/or night may provide sufficient data for analysis described herein. In some implementations, the ring 104 may continuously acquire the PPG signal (e.g., at a sampling rate). In some examples, even though the PPG signal is collected continuously, the system 200 may leverage other information about the user that it has collected or otherwise derived (e.g., sleep stage, activity levels, illness onset, etc.) to select a representative PPG signal for a particular day that is an accurate representation of the underlying physiological phenomenon.

In contrast, systems that require a user to manually obtain their data signals each day and/or systems that acquire data signals continuously but lack any other contextual information about the user may select inaccurate or inconsistent data signals for their sleep age metric determinations, leading to inaccurate determinations and decreased user experience. In contrast, data collected by the ring 104 may be used to accurately determine the sleep age metric of the user. Determining the sleep age metric and related techniques are further shown and described with reference to FIGS. 3 and 4.

Figure 3:
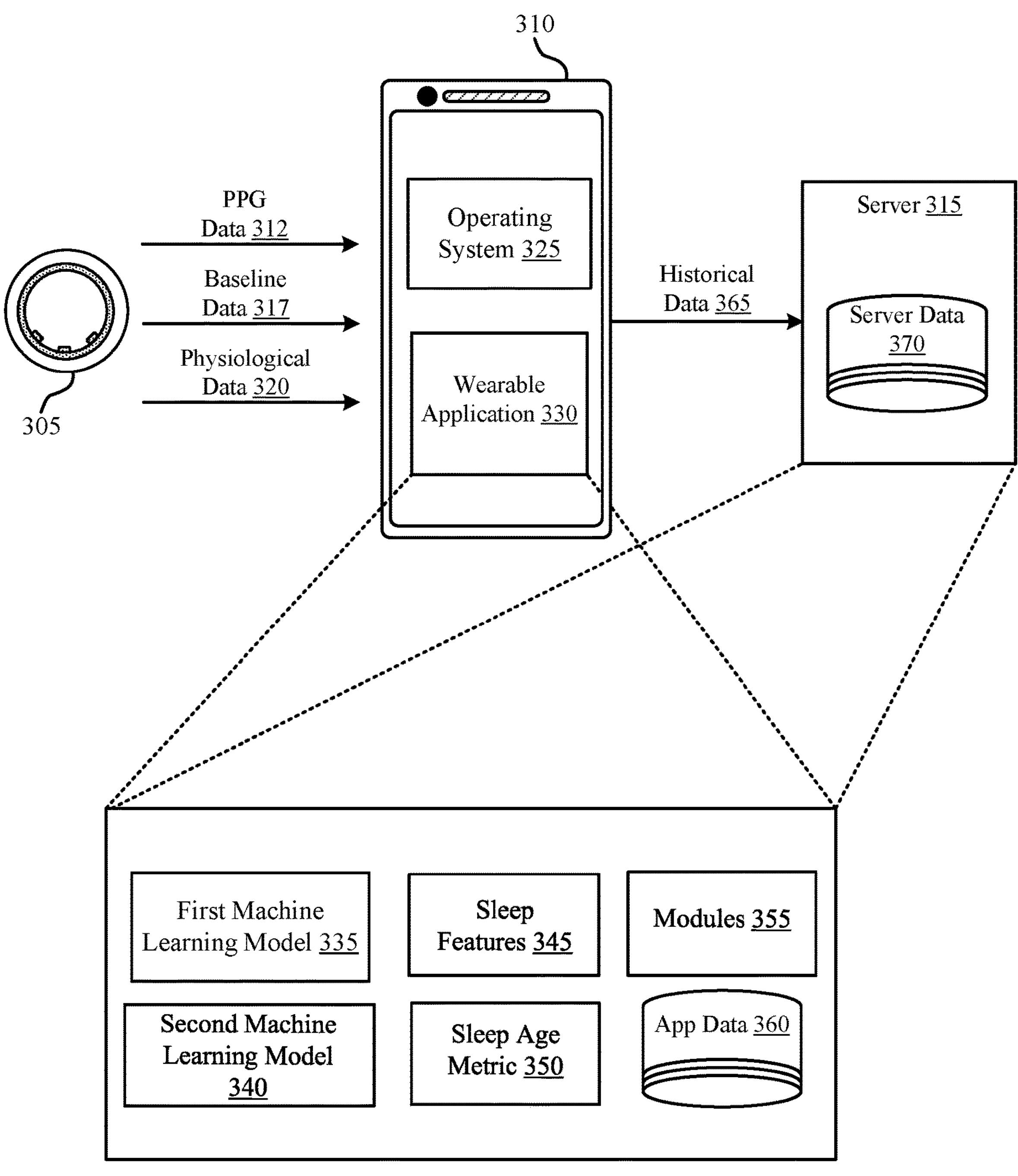
FIG. 3 shows an example of a system that supports sleep age determination from wearable-based physiological data in accordance with aspects of the present disclosure.

FIG. 3 shows an example of a system 300 that supports sleep age determination from wearable-based physiological data in accordance with aspects of the present disclosure. The system 300 may implement, or be implemented by, system 100, system 200, or both. In particular, system 300 illustrates an example of a ring 305 (e.g., wearable device 104), a user device 310, and a server 315, as described with reference to FIG. 1. Although the system may be implemented by a ring 305, a user device 310, and/or a server 315, any combination of computing devices described herein may implement the features attributed to the system 300.

The ring 305 may acquire PPG data 312 throughout a time interval that includes multiple sleep intervals during which the user is asleep. The ring 305 may transmit PPG data 312 to the user device 310, the server 315, or both. In some cases, multiple devices may acquire PPG data 312. For example, a first computing device (e.g., user device 310) and a second computing device (e.g., the ring 305) may acquire the PPG data 312. The system 300 (e.g., including the user device 310, the server 315, or both) may receive the PPG data 312 after the ring 305 measures the PPG data 312 from the user throughout the time interval that the user is asleep. For example, the ring 305 may acquire raw PPG data 312 and convert the raw PPG data to features with varying granularity. In some cases, the ring 305 may send the PPG data 312 to another computing device, such as a mobile device (e.g., user device 310) for further processing.

The ring 305 may acquire physiological data 320 during the time interval that the user is asleep. The physiological data 320 may include temperature data, heart rate data, respiratory rate data, HRV data, SpO2 data, (e.g., blood oxygen saturation), among other forms of physiological data as described herein. The ring 305 may transmit physiological data 320 to the user device 310, the server 315, or both. The temperature data may include continuous nighttime temperature data. The respiratory rate data may include continuous nighttime breath rate data. In some cases, multiple devices may acquire physiological data 320.

In some cases, the ring 305 may acquire baseline data 317, such as baseline PPG data, baseline temperature data, baseline respiratory rate data, baseline heart rate data, baseline HRV data, baseline SpO2 data, and/or other user baseline physiological data. The ring 305 may transmit baseline data 317 to the user device 310 such that the user device and/or the server 315 may receive the baseline data 317 measured from the user via the ring 305. The baseline data 317 may be measured throughout a reference window that precedes the time interval that includes the plurality of sleep intervals during which the user is asleep. For example, the PPG data 312 may be measured from the user for the past month while the baseline data 317 may be measured from the user for the previous six months.

The baseline data 317 for the user is periodically updated based on subsequent measurements of the PPG data 312. For example, the baseline data 317 may be adjusted as the time interval including the sleep intervals changes over time. For example, the baseline data 317 may be calculated from the preceding months of data from the current calendar day. In such cases, the baseline data 317 may be automatically adjusted as the PPG data 312 is updated based on the time interval changing with the current calendar day.

The user device 310, the server 315, or both may identify, based on the baseline data 317, one or more actions engaged in by the user during the reference window, one or more environmental conditions associated with an environment of the user during the reference window, or both. In such cases, the system 300 may look at the user's actions and/or environmental conditions from the past to provide personalized insights to improve the user's sleep age. For example, the system 300 may determine that the user achieved more REM sleep throughout the night when the user lowered their room temperature at night. Thus, if poor REM sleep is affecting the user's sleep age, the system 300 may provide a recommendation to help the user improve their sleep age. By way of another example, the system 300 may be configured to determine, based on the baseline data 317, that the user achieves more deep sleep when the user takes walk and/or a cold shower shortly before bed (e.g., identify a relationship between increased deep sleep, and cold showers/walks before bed).

The baseline data 317 (e.g., temperature, heart rate, respiratory rate, HRV, sleep disturbances, SpO2, and the like) may be tailored specific to the user based on historical data 365 acquired by the system 300. For example, these baselines (e.g., baseline data 317) may represent baseline or average values of physiological parameters or typical trends of physiological values measured prior to the time interval including the plurality of sleep intervals that the user is asleep. In some cases, the baselines may differ throughout the period of measurement (e.g., based on the different stages of pregnancy, postpartum, illness, and/or other health-related events) for each physiological parameter. In some cases, the baselines may be based on known standards, averages among users, demographic-specific averages, and the like.

The system 300 may calculate baseline values for the user based on inputting the baseline data 317 into a machine learning model (e.g., the first machine learning model 335, the second machine learning model 340, or both). For example, the baseline data 317 may be calculated based on calculating an average temperature, heart rate, respiratory rate, HRV, SpO2 for a plurality of days (e.g., the past 30 days, the past 90 day's, etc.). In some cases, the baseline data 317 may be calculated based on calculating an average value for multiple time periods of the day. For example, the user's temperature may be calculated for each minute, hour, and the like of the calendar day. In some cases, the baseline data 317 may be calculated based on calculating a median value over the plurality of days. The machine learning model (e.g., the first machine learning model 335, the second machine learning model 340, or both) may classify the user's baseline data 317 according to average values or median values to determine the user's baseline data 317. In some examples, the system 300 may determine a time series of baseline data 317 values taken over the plurality of days that precedes the time interval including the plurality of sleep intervals.

In some cases, the system 300 may smooth the PPG data 312, the baseline data 317, the physiological data 320, or any combination thereof (e.g., using a 7-day smoothing window, a 90-day smoothing window, or other window). The missing values may be imputed (e.g., using the forecaster Impute method from the Python package). In some cases, the ring 305, the user device 310, and/or the servers 315 may be configured to normalize the collected physiological data 320, the PPG data 312, or both. For example, the ring 305, the user device 310, and/or the servers 315 may be configured to perform one or more normalization procedures on the collected physiological data 320, the PPG data 312, or both.

In some cases, physiological data 320 (e.g., features of the physiological data 320), PPG data 312 (e.g., features of the PPG data 312), or both may be normalized on a per-night basis. Normalization may account for inter-individual differences in features (e.g., nightly heart rate or HRV). While all parameters/features (e.g., temperature data, accelerometer data, heart rate data, HRV data, PPG data 312, and the like) may have some discriminatory power to detect different sleep stages, the physiological data 320 and PPG data 312 may be highly individual, and absolute values may differ greatly between individuals based on parameters other than those of interest (e.g., genetics, age, etc.). In some cases, the components may input the normalized physiological data 320, the PPG data 312, or both into the first machine learning model 335, the second machine learning model 340, or both.

The sleep staging classification procedure may be improved when normalizing features of the physiological data 320, the PPG data 312, or both, especially for HRV features. Feature normalization may be effective when using HRV features as the physiological principles behind using ANS activity for the sleep staging classification procedure due to the fact that there may be large differences in sympathetic and parasympathetic activity across sleep stages, and these differences may be identified within individuals as relative changes over time.

The system 300 may be configured to perform respective processing procedures described herein using different components of the system 300 in order to reduce a latency of data presented to the user, conserve processing resources, and the like. For example, processing procedures that are more time-sensitive (e.g., lower latency requirements) and/or less computationally expensive (e.g., calculation of Sleep/Readiness Scores) may be performed via the user device 310, whereas processing procedures that are less time-sensitive and/or more computationally expensive (e.g., sleep stage classification procedure) may be performed via the servers 315.

The user device 310 may include the wearable application 330 and an operating system 325. The wearable application 330 may run on the operating system 325 of a user device 310 and may be associated with the ring 305. The wearable application 330 may include a first machine learning model 335, a second machine learning model 340, sleep features 345 and sleep age metric 350. In some cases, the server 315 may include the first machine learning model 335, the second machine learning model 340, the sleep features 345, and the sleep age metric 350.

The system 300 (including the user device 310, the server 315, or both) may input, using one or more processors communicatively coupled with the ring 305, the PPG data 312 into the first machine learning model 335. Using the first machine learning model 335, the system may classify, as part of a sleep staging classification procedure, the PPG data 312 collected during the plurality of sleep intervals into a plurality of sleep stages. The plurality of sleep stages may include an awake sleep stage, a light sleep stage, a deep sleep stage, a REM sleep stage, or any combination thereof.

The system may input one or more sleep features 345 from the sleep staging classification procedure into the second machine learning model 340 based on classifying the PPG data 312. The one or more sleep features 345 may include at least a duration that the user spent in each of the plurality of sleep stages. Other sleep features 345 may include, but are not limited to, an average bedtime for the user, an average wake-time of the user, a sleep midpoint of the user, average HRV values of the user during the respective sleep stages, and the like. The second machine learning model 340 may output a sleep age metric 350 associated with a sleep health of the user relative to a chronological age of the user in response to inputting the one or more sleep features 345 into the second machine learning model 340. The system (e.g., the server 315) may transmit, to the user device 310 associated with the ring 305, an instruction to cause the GUI of the user device 310 to display an indication of the sleep age metric 350 and an insight for a value of the sleep age metric 350 that is based on the one or more sleep features 345.

The sleep age metric 350 may be an example of a longer-term sleep age metric that is calculated based on the user's sleep data averaged over weeks and months of data. The sleep age metric 350 may give users a longer-term, holistic view of their sleep health. The sleep age metric 350 may be associated with health and mortality outcomes. The system 300 may use network security situation assessment (NSSA) and longer time periods of data over a plurality of weeks and/or months to calculate the sleep age metric 350.

In some cases, the system 300 may identify deviations between the calculated sleep age metric 350 and the user's chronological age (e.g., the user is 25 (chronological age=25), but the user's sleep age is 32). The system 300 may determine whether the deviations are associated with health outcomes and identify which health outcomes are associated with the deviations. For example, the system 300 may determine that the user's calculated sleep age metric 350 is greater than the chronological age of the user and determine that the deviation is based on the user's total amount of sleep.

In some cases, the user device 310, the server 315, or both may determine one or more relationships between the one or more sleep features 345 and the one or more actions engaged in by the user during the reference window, the one or more environmental conditions associated with an environment of the user during the reference window. The insight may be based on the one or more relationships. In some cases, the one or more relationships may include a relationship between the one or more actions, the one or more environmental conditions, or both, and a change in the duration that the user spent in one or more of the plurality of sleep stages during the reference window.

The system 300 may learn what actions and/or conditions increased the amount of time a user spent in a certain sleep stage. In such cases, the system 300 may look at user's actions and/or environmental conditions from the past to provide personalized insights to improve the user's sleep age metric 350 (e.g., when the user took hot showers before bed, the user's total amount of sleep increased). Thus, if the total amount of sleep is affecting the user's sleep age metric 350, the system may make the recommendation to take hot showers to help improve their sleep age metric 350.

In some cases, the physiological data 320 may be inputted into the second machine learning model 340 based on receiving the physiological data 320. In this regard, the second machine learning model 340 may be configured to determine the sleep age metric based on (1) sleep features, and (2) the raw/filtered/normalized physiological data 320. For example, at least the temperature data, the heart rate data, the HRV data, and the like may be inputted into the second machine learning model 340 based on receiving the physiological data 320. In such cases, the sleep age metric 350 may be based on inputting the temperature data, the heart rate data, the HRV data, and the like into the second machine learning model 340.

The wearable application 330 may include at least modules 355 and application data 360. In some cases, the application data 360 may include historical physiological data patterns for the user and other data. The physiological data patterns may include temperature data, heart rate data, respiratory rate data, HRV data, blood oxygen saturation data, PPG data, or a combination thereof.

The wearable application 330 or the server 315 may calculate the sleep age metric 350. The wearable application 330 may present the sleep age metric 350 to the user. The wearable application 330 may include an application data processing module that may perform data processing. For example, the application data processing module may include modules 355 that provide functions attributed to the system 300. Example modules 355 may include a sleep feature module, a sleep age metric module, and the like.

The sleep feature module may classify, as part of the sleep staging classification procedure and using the first machine learning model 335, the PPG data 312 collected during the plurality of sleep intervals into a plurality of sleep stages. The sleep feature model may input one or more sleep features from the sleep staging classification procedure into the second machine learning model 340 based on classifying the PPG data 312. The sleep age metric target module may output, from the second machine learning model 340, a sleep age metric associated with a sleep health of the user relative to a chronological age of the user. In such cases, the system 300 may receive user physiological data 320 and PPG data 312 from a ring 305 and output the sleep features 345 and sleep age metric 350. The wearable application 330 may store application data 360, such as acquired physiological data 320, PPG data 312, and baseline data 317.

In some cases, the user's logged symptoms (e.g., tags) in combination with the user's physiological data 320 and/or PPG data 312 may characterize the sleep age metric 350. In such cases, the user's logged inputs (e.g., tags) may contribute to calculating the sleep age metric 350. The logged user inputs may be an example of information associated with a health record of the user (e.g., previous surgeries, pregnancies, illnesses, medications, and the like).

The system 300 may cause a GUI of the user device 310 to display the sleep age metric 350. The system 300 may generate a message for display on a GUI on the user device 310 that indicates the sleep age metric 350. The calculation and/or adjustment to the sleep age metric 350 may trigger a personalized message to a user highlighting the educational content associated with the sleep age metric 350. In some cases, the message may include recommendations to improve the sleep age metric 350, a recommendation to exercise, an adjusted set of sleep targets, an adjusted set of activity targets, one or more explanations for a difference between the sleep age metric 350 and the chronological age of the user where the one or more explanations are associated with the one or more sleep features 345, a rationale for the value of the sleep age metric 350, trends associated with the sleep age metric 350, educational content associated with the sleep age metric 350, or a combination thereof.

In some implementations, the wearable application 330 may notify the user of the sleep age metric 350 and/or prompt the user to perform a variety of tasks in the activity GUI. The notifications and prompts may include text, graphics, and/or other user interface elements. In some cases, the wearable application 330 may display notifications and prompts when there is a change in the sleep age metric 350. The user device 310 may display notifications and prompts in a separate window on the home screen and/or overlaid onto other screens (e.g., at the very top of the home screen). In some cases, the user device 310 may display the notifications and prompts on a mobile device, a user's watch device, or both.

The message may provide an assessment of the sleep age metric 350. For example, as the user ages, the sleep patterns change (e.g., less deep sleep, more interrupted sleep, less sleep in total, etc.), and the sleep age metric 350 may indicate how the sleep age metric 350 is changing and what factors contribute to the sleep age metric 350. The sleep age metric 350 may be a value that represents the comparison of the user's sleep age to the user's chronological age. The difference between the sleep age metric 350 and the user's chronological age may be predictive of future health outcomes, as described herein.

In some implementations, the user device 310 may store historical user data 365. The historical data 365 may include historical temperature patterns of the user, historical heart rate patterns of the user, historical respiratory rate patterns of the user, historical HRV patterns of the user, historical sleep data, historical blood oxygen saturation of the user, or a combination thereof. The historical data 365 may be selected from the last few months. The historical data 365 may be used (e.g., by the user device 310 or server 315) to calculate the sleep age metric 350. The historical data 365 may be used by the server 315. Using the historical data 365 may allow the user device 310 and/or server 315 to personalize the GUI by taking into consideration the user's historical data 365. In some cases, the historical data 365 may be an example of the baseline data 317.

The user device 310 may transmit historical data 365 to the server 315. In some cases, the transmitted historical data 365 may be the same historical data stored in the wearable application 330. In other examples, the historical data 365 may be different than the historical data stored in the wearable application 330. The server 315 may receive the historical data 365. The server 315 may store the historical data 365 in server data 370.

In some implementations, the user device 310 and/or server 315 may also store other data that may be an example of user information. The user information may include, but is not limited to, user age, weight, height, body mass index, gender, and medical history of the user. In some implementations, the user information may be used as features for calculating the sleep age metric 350. The server data 370 may include the other data such as user information.

Figure 4:
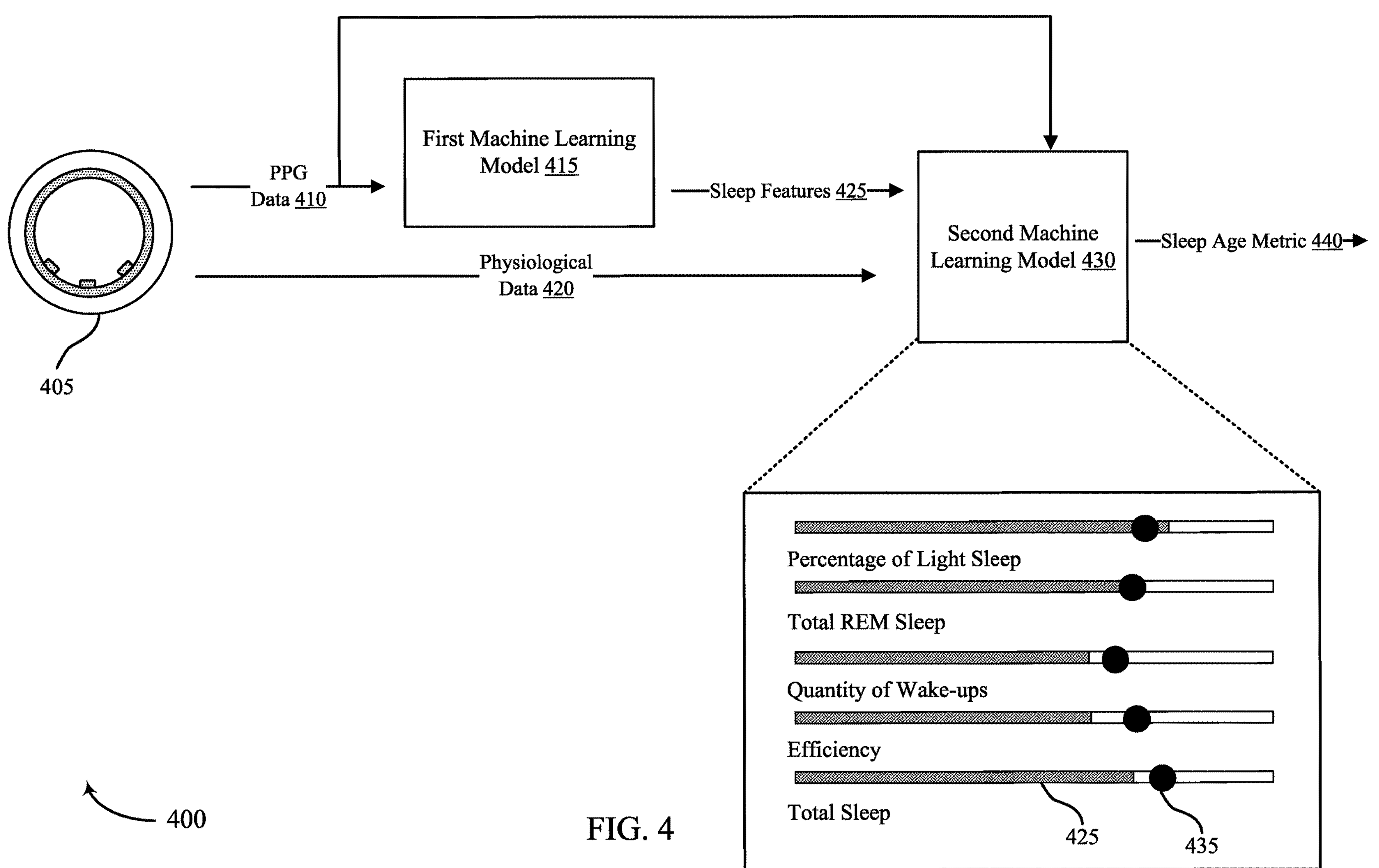
FIG. 4 shows an example of a system that supports sleep age determination from wearable-based physiological data in accordance with aspects of the present disclosure.

FIG. 4 shows an example of a system 400 that supports sleep age determination from wearable-based physiological data in accordance with aspects of the present disclosure. The system 400 may implement, or be implemented by, system 100, system 200, system 300, or a combination thereof. In particular, system 400 illustrates an example of a ring 405 (e.g., wearable device 104), a first machine learning model 415, and a second machine learning model 430, as described with reference to FIGS. 1-3.

The system 400 (e.g., including at least the first machine learning model 415 and/or the second machine learning model 43) may receive PPG data 410 measured from the user by the ring 405 throughout the time interval including the plurality of sleep intervals during which the user is asleep. For example, the ring 405 may measure the PPG data 410 from the user throughout the time interval that the user is asleep. The first machine learning model 415 may receive the PPG data 410 and, in response, the PPG data 410 may be inputted into the first machine learning model 415 using one or more processors communicatively coupled with the ring 405.

The first machine learning model 415 may include any machine learning classifier or algorithm known in the art including, but not limited to, a Random Forest classifier, a Naïve Bayes classifier, a deep learning classifier, an artificial neural network, and the like. In some cases, machine learning model training and testing may be performed using a Light Gradient BoostingMachine (LightGBM) classifier, with a DART boosting and 500 estimators. LightGBM may provide high accuracy, fast training, low memory usage, and may be capable of handling missing values when data quality is too poor to calculate features. Moreover, the first machine learning model 415 may be implemented by the ring 405, a user device 106, a server 110, or any combination thereof.

As part of a sleep staging classification procedure, the first machine learning model 415 may classify the PPG data 410 collected during the plurality of sleep intervals into a plurality of sleep stages. The plurality of sleep stages may include an awake sleep stage, a light sleep stage, a deep sleep stage, a REM sleep stage, or any combination thereof. For example, portions of the PPG data 410 may indicate that the user is experiencing a light sleep stage, and other portions of the PPG data 410 may indicate the user is experiencing a deep sleep stage, a REM sleep stage, or an awake sleep stage. The frequency, amplitude, or both of the PPG data 410 received may indicate which of the plurality of sleep stages the user is experiencing. In such cases, an increased frequency of the PPG data 410 may indicate the user is experiencing a REM sleep stage while a decreased frequency of the PPG data 410 may indicate that the user is experiencing a deep sleep stage.

In some cases, the first machine learning model 415 may extract one or more sleep features 425 from the sleep staging classification procedure. The one or more sleep features 425 may include at least a duration that the user spent in each of the plurality of sleep stages. In some cases, the sleep features 425 may include a percentage of time that the user spent in each of the plurality of sleep stages, a sleep efficiency, a quantity of times that the user transitioned between the plurality of sleep stages, a quantity of times that the user woke up during the plurality of sleep intervals, or a combination thereof. In some examples, the sleep features 425 may include a sleep midpoint of the plurality of sleep intervals, a bed time that the user went to sleep for the plurality of sleep intervals, an awake time that the user woke up from the plurality of sleep intervals, a total time that the user spent sleeping during the plurality of sleep intervals, or a combination thereof.

The sleep features 425 may be inputted into the second machine learning model 430 in response to classifying the PPG data 410. In some examples, the PPG data 410 (e.g., raw PPG data) may be inputted into the second machine learning model 430 in addition to the one or more sleep features 425. In such cases, the inputs to the second machine learning model 430 may include the sleep features 42,5 or both the PPG data 410 and the sleep feature 425. The system 400 may determine the user's sleep age metric 440 in response to inputting the sleep features 425 into the second machine learning model 430. In some cases, the system 400 may determine the user's sleep age metric 440 in response to inputting both the PPG data 410 and the sleep features 425 into the second machine learning model 430.

In some cases, the system 400 may input other features of raw data (e.g., physiological data 420) into the second machine learning model 430 to determine the user's sleep age metric 440. For example, the second machine learning model 430 may receive physiological data 420. The physiological data may include at least temperature data, heart rate data, HRV data, respiratory data, SpO2 data, and the like. The system 400 may input the physiological data 420 into the second machine learning model 430 in response to receiving the physiological data 420. In such cases, the system 400 may output the sleep age metric 440 based on inputting the physiological data 420 into the second machine learning model 430.

For example, the system 400 may receive temperature data, heart rate data, HRV data, or a combination thereof measured from the user by the wearable device when the user is asleep. The system 400 may input the temperature data, heart rate data, HRV data, or a combination thereof into the second machine learning model 430 based on receiving the respective physiological data 420. In such cases, the system 400 may output the sleep age metric 440 after inputting the respective physiological data 420 into the second machine learning model 430.

The second machine learning model 430 may include any machine learning classifier or algorithm known in the art including, but not limited to, a Random Forest classifier, a Naïve Bayes classifier, a deep learning classifier, an artificial neural network, and the like. In some aspects, machine learning model training and testing may be performed using a Light Gradient BoostingMachine (LightGBM) classifier, with a DART boosting and 500 estimators. Moreover, The second machine learning model 430 may be implemented by the ring 405, a user device 106, a server 110, or any combination thereof.

In some cases, the first machine learning model 415, the second machine learning model 430, or both, may be trained on the user's physiological data 420, the PPG data 410, or both. The first machine learning model 415, the second machine learning model 430, or both, may be trained on a data set from a plurality of users (e.g., fifty thousand users) to determine the baseline sleep features 435 associated with each chronological age of the user. That is, the baseline sleep features 435 for a 25 year old user may be different than baseline sleep features 435 for a 40 year old user.

The second machine learning model 430 may be trained on outputs from the first machine learning model 415. For example, the second machine learning model 430 may be trained on the sleep features 425, the physiological data 420, the PPG data 410, or a combination thereof. The first machine learning model 415, the second machine learning model 430, or both may be trained based on the insight for the value of the sleep age metric 440. For example, the system 400 may train the machine learning models because the insight may indicate that the value of the sleep age metric 440 is based on the user's deep sleep, REM sleep, and the like.

The first machine learning model 415, the second machine learning model 430, or both, may be optimized to minimize mean squared error (MSE). The first machine learning model 415, the second machine learning model 430, or both, may implement a hyperparameter tuning loop that uses Bayesian optimization to minimize the average mean absolute error (MAE). The hyperparameters may include, for some models, parameters controlling sample weights that weight observations at the tails of the age distribution more heavily where the sample weight for an observation is the inverse proportion of that observation's five year age bucket in the training set raised to a power. The power may be a model hyperparameter. In some cases, the system 400 may implement a custom loss function that takes the covariance of the residuals and age into account to help correct for regression to the mean.

The system 400 may compare the one or more sleep features 425 from the sleep staging classification procedure with one or more baseline sleep features 435 associated with the chronological age of the user. That is, the system 400 may compare, using the second machine learning model 430, inputted sleep staging features (e.g., sleep features 425) to the user's baseline sleep staging features (e.g., baseline sleep features 435). For example, the system 400 may compare how long the user spent in REM sleep to the average amount of time that other people of the user's same/similar age spend in REM sleep, compare the user's total amount of sleep to the average amount of time people of the user's age sleeps, or both. In other examples, the system 400 may compare the user's sleep efficiency to an average sleep efficiency for people of the user's age, the user's percentage of light sleep to an average percentage that people of the user's age spends in light sleep, an amount of wake-ups the user experienced to an average amount of wake-ups for people of the user's age, and the like.

In some cases, the system 400 may compare the sleep features 425 with the baseline sleep features 435 in response to inputting the one or more sleep features 425 into the second machine learning model 430. In such cases, the system 400 may output the sleep age metric 440 based on comparing the one or more sleep features 425 with the one or more baseline sleep features 435. The system 400 may identify the user's chronological age, identify the sleep age metric 440, and perform a comparison of the user's chronological age to the sleep age metric 440. In some cases, the system 400 may determine how a user's sleep changes with age. For example, the system 400 may identify that the user's sleep efficiency is lower than the sleep efficiency for a user's chronological age.

In some cases, the system 400 may predict the sleep age metric 440 using linear regression of the one or more sleep features 425. For example, the system 400 may utilize a one day aggregation of the sleep features 425, a seven day aggregation of the sleep features 425, a 30 day aggregation of the sleep features 425, a 90 day aggregation of the sleep features 425, or a combination thereof. The aggregations of the sleep features 425 may include at least a mean of each sleep feature 425, a standard deviation of each sleep feature 425, or both. For example, the system 400 may calculate the mean and/or standard deviation of each of the sleep features 425 over the past 30 day's or 90 days. In some cases, the linear regression model may include penalized linear regression (e.g., with and without second-degree polynomial combinations of the features) and LightGBM models, as described herein.

The second machine learning model 430 may output the sleep age metric 440 and a reasoning and/or insight into why the sleep age metric 440 is above, below, or equal to the user's chronological age. In such cases, the system 400 may enable the user to identify and understand why a user's sleep age was calculated the way it was whereas other sleep age studies are not able to tell the user why they have a poor, average, or optimal sleep age metric.

In particular, by utilizing sleep features 425 as an input to the second machine learning model 430, techniques described herein may be able to answer the question as to "why" a user's sleep age was calculated the way it was. As such, techniques described herein may provide users with more accurate and actionable guidance to improve their sleep age metric as compared to some conventional approaches for determining a user's sleep age.

For example, as described previously herein, some sleep studies calculate sleep health metrics by inputting raw signals (e.g., raw PSG and/or EEG data) into machine learning models. Such sleep studies typically utilize only a single night's worth of data, and therefore provide a very limited snapshot into the user's overall health. Moreover, because such sleep studies determine sleep health metrics based on raw signals, such sleep studies may be unable to answer "why" the user's sleep health metrics are calculated the way they were, as the models may only be trained to recognize certain patterns or characteristics within the raw PSG signals.

Comparatively, techniques described herein may train the second machine learning model 430 to determine sleep age metrics based on the sleep features 425 (in the addition to, or in the alternate to, raw PPG data 410). By training the second machine learning model 430 on the sleep features 425, the second machine learning model 430 may be able to determine which specific sleep features 425 are the primary factors for the user's high or low sleep age metric. That is, the second machine learning model 430 may be able to identify specific sleep features 425 that are the primary source for any deviation between the user's sleep age and their chronological age. As such, techniques described herein may provide the user with more actionable guidance to adjust their sleeping habits to change their sleep features 425, and thereby improve their sleep age metric 440.

Figure 5A:
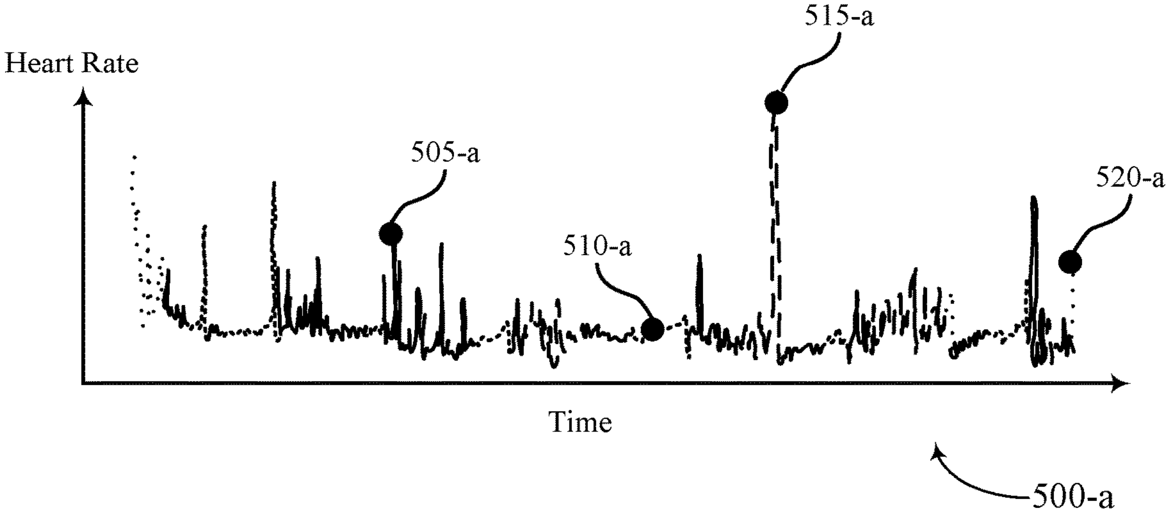
FIG. 5A shows an example of a heart rate data diagram that supports sleep age determination from wearable-based physiological data in accordance with aspects of the present disclosure.

FIG. 5A shows an example of a heart rate data diagram 500-*a* that supports sleep age determination from wearable-based physiological data in accordance with aspects of the present disclosure. The heart rate data diagram 500-*a* may implement, or be implemented by, system 100, system 200, system 300, system 400, or a combination thereof.

As described herein, the physiological data (e.g., the heart rate data) may be classified into a plurality of sleep stages. For example, the heart rate data measured during the time interval may be pattern coded or otherwise labeled as being associated with a respective sleep stage (e.g., awake sleep stage, light sleep stage, REM sleep stage, deep sleep stage). Heart rate data diagram 500-*a* may be an example of heart rate data measured from the user by the wearable device throughout the time interval including the plurality of sleep intervals during which the user is asleep. In some cases, the time interval may be an example of the previous night's sleep or an average heart rate data from multiple previous night's sleep (e.g., the past three days, the past 30 days, or the like).

The system (e.g., ring, user device, and/or servers) may be configured to classify the physiological data (e.g., the heart rate data) using the machine learning classifiers (e.g., the first machine learning model and/or the second machine learning model). In particular, the system may be configured to classify the heart rate data into at least one sleep stage of a set of sleep stages (e.g., awake sleep stage, light sleep stage, REM sleep stage, deep sleep stage) for at least a portion of the time interval that physiological data (e.g., sleep data) was collected. That is, the system may be configured to identify sleep intervals (e.g., periods of time the user was asleep) for the user and may classify each respective sleep interval into one of an awake sleep stage, a light sleep stage, a REM sleep stage, or a deep sleep stage. In such cases, the system may be configured to classify periods of awake, light, REM, and deep sleep for the user.

In some cases, the components of the system may be configured to extract features from the physiological data (e.g., including at least the heart rate data). The system may compare the heart rate data from the plurality of sleep stages with baseline heart rate data that the user is awake (e.g., morning heart rate data 520-*a*). In some case, the system may compare the heart rate data from the plurality of sleep stages with baseline heart rate data in response to inputting the heart rate data into the second machine learning model. In such cases, the system may output the sleep age metric based on comparing the heart rate data with the baseline heart rate data.

The system may compare the heart rate data in different sleep stages to the morning heart rate data 520-*a*. For example, the system may compare light sleep stage heart rate data 505-*a* to the morning heart rate data 520-*a* to determine the sleep age metric. In other examples, the system may compare deep sleep stage heart rate data 510-*a* to the morning heart rate data 520-*a* to determine the sleep age metric, compare the REM stage heart rate data 515-*a* to the morning heart rate data 520-*a* to determine the sleep age metric, or both. In such cases, the system may combine the raw features (e.g., heart rate data during different sleep stages) with the sleep staging algorithm features (e.g., sleep features) to determine the sleep age.

In other examples, the system may compare the heart rate data from one of the plurality of sleep stages with the heart rate data from another one of the plurality of sleep stages. In some cases, the system may compare the heart rate data from one of the plurality of sleep stages with heart rate data from another one of the plurality of sleep stages in response to inputting the heart rate data into the second machine learning model. In such cases, the system may output the sleep age metric based on comparing the heart rate data from one of the plurality of sleep stages with heart rate data from another one of the plurality of sleep stages. For example, the system may compare light sleep stage heart rate data 505-*a* to the deep sleep stage heart rate data 510-*a*, the REM stage heart rate data 515-*a*, or both to determine the sleep age metric. In other examples, the system may compare deep sleep stage heart rate data 510-*a* to the REM stage heart rate data 515-*a* to determine the sleep age metric.

Figure 5B:
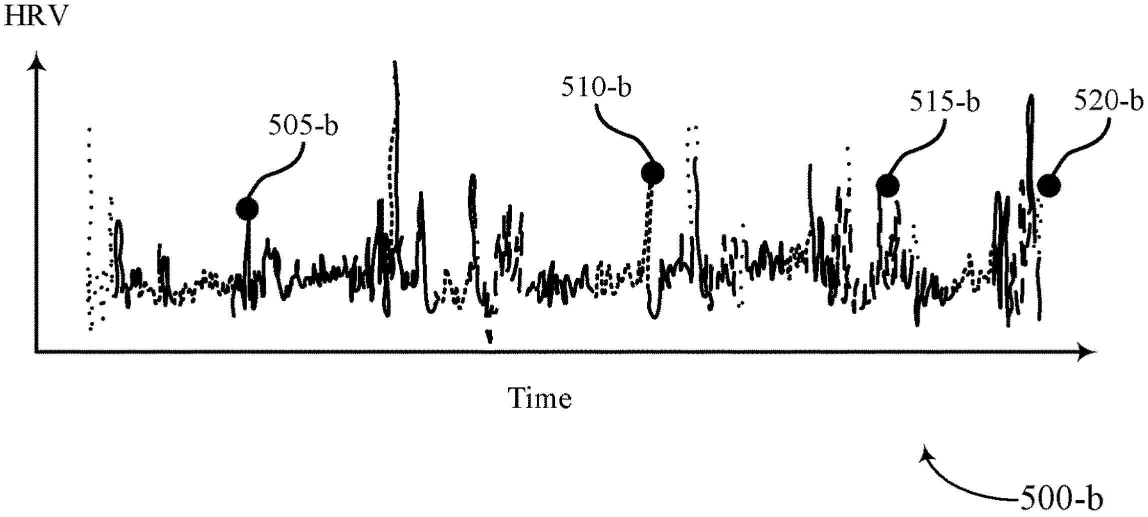
FIG. 5B shows an example of a heart rate variability (HRV) data diagram that supports sleep age determination from wearable-based physiological data in accordance with aspects of the present disclosure.

FIG. 5B illustrates an example of a HRV data diagram 500-*b* that supports sleep age determination from wearable-based physiological data in accordance with aspects of the present disclosure. The HRV data diagram 500-*b* may implement, or be implemented by, system 100, system 200, system 300, system 400, or a combination thereof.

As described herein, the physiological data (e.g., the HRV data) may be classified into one sleep stage of the plurality of sleep stages. For example, the HRV data measured during the time interval may be pattern coded or otherwise labeled as being associated with a respective sleep stage (e.g., awake sleep stage, light sleep stage, REM sleep stage, deep sleep stage). HRV data diagram 500-*b* may be an example of HRV data measured from the user by the wearable device throughout the time interval including the plurality of sleep intervals during which the user is asleep. In some cases, the time interval may be an example of the previous night's sleep or an average HRV data from multiple previous night's sleep (e.g., the past three days, the past 30 days, or the like).

The system (e.g., ring, user device, and/or servers) may be configured to classify the HRV data using the machine learning classifiers (e.g., the first machine learning model and/or the second machine learning model). In particular, the system may be configured to classify the HRV data into at least one sleep stage of a set of sleep stages (e.g., awake sleep stage, light sleep stage, REM sleep stage, deep sleep stage) for at least a portion of the time interval that physiological data (e.g., sleep data) was collected.

In some cases, the components of the system may be configured to extract features from the HRV data. In some examples, the system may compare the HRV data from the plurality of sleep stages with baseline HRV data that the user is awake (e.g., morning HRV data d520-*b*). In some cases, the system may compare the HRV data from the plurality of sleep stages with baseline HRV data in response to inputting the HRV data into the second machine learning model. In such cases, the system may output the sleep age metric based on comparing the HRV data with the baseline HRV data.

The system may compare the HRV data in different sleep stages over night to the morning HRV data 520-*b*. For example, the system may compare light sleep stage HRV data 505-*b* to the morning HRV data 520-*b* to determine the sleep age metric. In other examples, the system may compare deep sleep stage HRV data 510-*b* to the morning HRV data 520-*b* to determine the sleep age metric, compare the REM stage HRV data 515-*b* to the morning HRV data 520-*b* to determine the sleep age metric, or both. In such cases, the system may combine the raw features (e.g., HRV data during different sleep stages) with the sleep staging algorithm features to determine the sleep age.

In other examples, the system may compare the HRV data from one of the plurality of sleep stages with the HRV data from another one of the plurality of sleep stages in response to inputting the HRV data into the second machine learning model. In such cases, the system may output the sleep age metric based on comparing the HRV data from one of the plurality of sleep stages with HRV data from another one of the plurality of sleep stages. For example, the system may compare light sleep stage HRV data 505-*b* to the deep sleep stage HRV data 510-*b*, the REM stage HRV data 515-*b*, or both to determine the sleep age metric. In other examples, the system may compare deep sleep stage HRV data 510-*b* to the REM stage HRV data 515-*b* to determine the sleep age metric.

Figure 6:
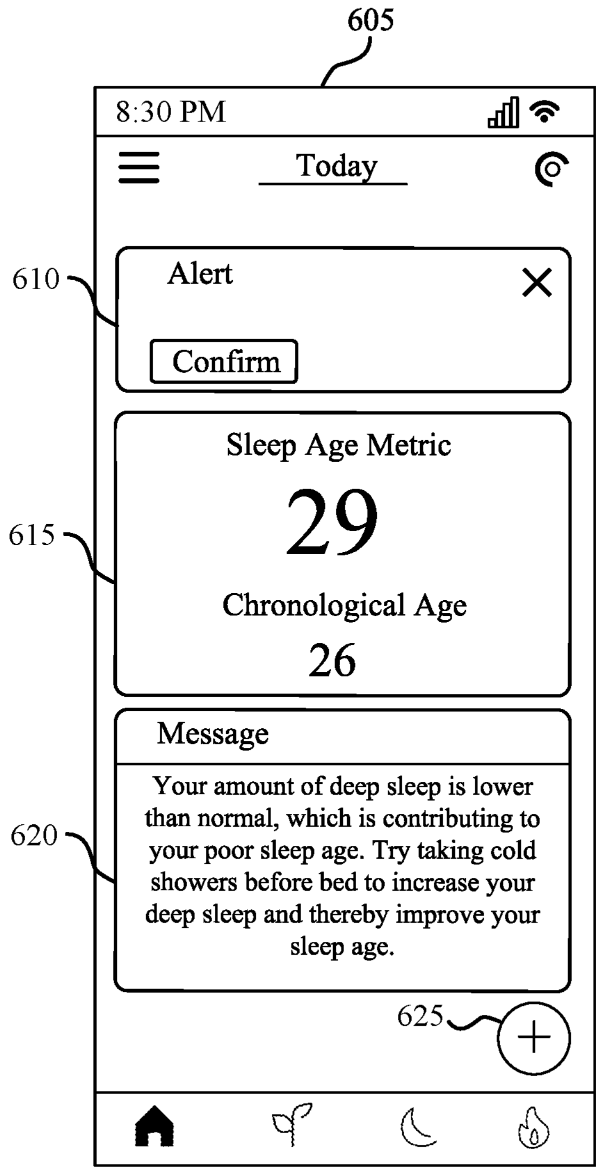
FIG. 6 shows an example of a graphical user interface (GUI) that supports sleep age determination from wearable-based physiological data in accordance with aspects of the present disclosure.

As described herein with reference to FIG. 6, the servers may cause the user device to display the heart rate data, HRV data, and/or other data determined/identified by the system to a user. For example, the user device may display, via the GUI, raw and/or pre-processed HRV data, heart rate data, or both collected by the ring, including at least the HRV data diagram 500-*b* and heart rate data diagram 500-*a*. In such cases, the user device may display the sleep intervals that have been classified with the corresponding sleep stages. That is, the user device may display, via the GUI, the sleep intervals and the classified sleep stage corresponding to each respective sleep interval.

FIG. 6 shows an example of a GUI 600 that supports sleep age determination from wearable-based physiological data in accordance with aspects of the present disclosure. The GUI 600 may implement, or be implemented by, aspects of the system 100, system 200, system 300, system 400, timing diagram 500, or any combination thereof. For example, the GUI 600 may be an example of a GUI 275 of a user device 106 (e.g., user device 106-*a*, 106-*b*, 106-*c*) corresponding to a user 102. In some examples, the GUI 600 illustrates a series of application pages 605 which may be displayed to a user via the GUI 600 (e.g., GUI 275 illustrated in FIG. 2).

The server of the system may generate a message 620 for display on the GUI 600 on a user device that indicates the indication of the sleep age metric. For example, the server of system may cause the GUI 600 of the user device (e.g., mobile device) to display a message 620, an alert 610, and/or a sleep age card 615 associated with the indication of the sleep age metric (e.g., via application page 605). In such cases, the system may output the indication of the sleep age metric on the GUI 600 of the user device to indicate a sleep health of the user relative to a chronological age of the user.

Upon determining the indication of the sleep age metric of the user, the user may be presented with the application page 605 upon opening the wearable application. As shown in FIG. 6, the application page 605 may display the indication that the sleep age metric is determined and/or identified via message 620 and/or sleep age card 615. In such cases, the application page 605 may include the message 620, the sleep age card 615, or both on the home page. In some cases, the sleep age card 615 may not be presented to the user every day upon opening the application page 605 but rather the sleep age card 615 may be included within a trends tab or another feature that shows the sleep age metric in the context of longer-term patterns. In cases where a user's sleep age metric is determined and/or identified, as described herein, the server may transmit an indication (e.g., message 620) to the user, where the message 620 is associated with the sleep age metric.

For example, the user may receive message 620, which may indicate trends associated with the sleep age metric, educational content associated with the sleep age metric, an adjusted set of sleep targets, an adjusted set of activity targets, recommendations to improve the sleep age metric, and the like. The messages 620 may be configurable/customizable, such that the user may receive different messages 620 based on the determination of the sleep age metric, as described previously herein. For example, the instruction transmitted to the user device that is configured to cause the GUI 600 to display the rationale for the value of the sleep age metric may include the recommendations to improve the sleep age metric, the trends associated with the sleep age metric, the educational content associated with the sleep age metric, the adjusted set of activity targets, the adjusted set of sleep targets, or a combination thereof. In such cases, the system provides actionable insights to improve the sleep age of the user.

In some cases, the message 620 may include weekly or monthly reports associated with the determined sleep age metric. The reports may indicate the trends associated with the sleep age metric. For example, the trends may indicate if the sleep age metric is changing (e.g., increasing or decreasing) relative to the previously determined sleep age metric. In some cases, the system may provide personalized recommendations to improve or maintain the sleep age metric. For example, the message 620 may indicate "Did you know that exercising four times a week can impact your sleep age metric? Try adding in some exercise this week."

In such cases, the message 620 may include insights, recommendations, and the like associated with the determined sleep age metric. The server of the system may cause the GUI 600 of the user device to display a message 620 associated with the sleep age metric. For example, the system may transmit, to the user device associated with the wearable device, an instruction to cause the GUI 600 of the user device to display an indication of the sleep age metric and an insight for a value of the sleep age metric. The user device may display recommendations and/or information associated with the sleep age metric via message 620. As noted previously herein, an accurately determined sleep age metric may be beneficial to a user's overall health.

Additionally, in some implementations, the application page 605 may display one or more scores (e.g., Sleep Score, Readiness Score, Activity Score, etc.) for the user for the respective day. Moreover, in some cases, the determined sleep age metric may be used to update (e.g., modify) one or more scores associated with the user (e.g., Sleep Score, Readiness Score, etc.). That is, data associated with the sleep age metric may be used to update the scores for the user for the following calendar days. In such cases, the system may notify the user of the score update via alert 610. In some cases, the Readiness Score may be updated based on the sleep age metric. In such cases, the Readiness Score may indicate to the user to "pay attention" based on the determined sleep age metric. If the Readiness Score changes for the user, the system may implement a recovery mode for users that may benefit from adjusted activity and readiness guidance for a couple of days, weeks, or months.

The message 620 may include the insight for the value of the sleep age metric. In some cases, the insight for the value of the sleep age metric may include one or more explanations for a difference between the sleep age metric and the chronological age of the user where the explanations are associated with one or more sleep features. The one or more sleep features may include a percentage of time that the user spent in each of the plurality of sleep stages, a sleep efficiency, a quantity of times that the user transitioned between the plurality of sleep stages, a quantity of times that the user woke up during the plurality of sleep intervals, a sleep midpoint of the plurality of sleep intervals, a bed time that the user went to sleep for the plurality of sleep intervals, an awake time that the user woke up from the plurality of sleep intervals, a total time that the user spent sleeping during the plurality of sleep intervals, or a combination thereof. For example, the insight (e.g., message 620) may indicate "Your deep sleep is lower than expected, which led to your sleep age being higher than your chronological age." In other examples, the insight may indicate "Your sleep efficiency and the total time you spent sleeping is above average which led to your sleep age metric being lower than your chronological age."

In other examples, the system may determine that the determined sleep age metric (e.g., sleep age) of the user is less than or equal to the chronological age of the user and may adjust the Readiness Score, Sleep Score, and/or Activity Score to accommodate the equal to (e.g., expected) or lower sleep age metric. In other cases, the system may determine that the determined sleep age metric (e.g., sleep age) of the user is greater than the chronological age of the user and may adjust the Readiness Score, Sleep Score, and/or Activity Score to offset the effects of the higher sleep age metric. In some cases, the system may provide insights to maintain the user's sleep age (e.g., sleep age metric) at an age lower than or the same as the user's chronological age. For example, the system may display, via message 620, recommendations and/or motivations for healthy habits and provide behavioral insights to the users. The sleep age card 615 may indicate the sleep age metric and the chronological age of the user. For example, the sleep age card 615 may indicate a sleep age metric of 29 that is higher than the chronological age of 26 of the user.

In some cases, the messages 620 displayed to the user via the GUI 600 of the user device may indicate how the determined sleep age metric affected the overall scores (e.g., overall Readiness Score) and/or the individual contributing factors. For example, a message 620 may indicate "It looks like your sleep age metric is greater than your chronological age, but implanting a more consistent bedtime routine can improve your sleep age metric" or "You sleep age metric looks like you are right on track with your chronological age. Keep up the great work!" In cases where the sleep age metric is determined to be higher than the chronological age, the messages 620 may provide suggestions for the user in order to improve their general health (e.g., including their sleep age metric). In such cases, the messages 620 displayed to the user may provide targeted insights to help the user adjust their lifestyle. For example, a message 620 may indicate "Your amount of deep sleep is lower than normal, which is contributing to your poor sleep age. Try taking cold showers before bed to increase your deep sleep and thereby improve your sleep age."

In some cases, the application page 605 may indicate one or more parameters, including the pulse waveform (e.g., a portion of the PPG signal), a temperature, heart rate, HRV, respiratory rate, sleep data, and the like via a graphical representation. The graphical representation may be an example of the graphical representation 445 or timing diagram 500 as described with reference to FIGS. 4 and 5. In such cases, the system may cause the GUI 600 of a user device to display a message 620, alert 610, or graphical representation associated with the sleep age metric.

In some cases, the user may log symptoms or events via user input 625. For example, the system may receive user input (e.g., tags) to log symptoms and/or events associated with illness, stress, pregnancy, or the like. For example, the system may receive an indication, via user input 625, of data related to a health record of the user. The data related to the health record of the user may include the indication of illness, stress, pregnancy, alcohol use, exercise history, sleep habits, current medications, previous surgeries, and the like. In other examples, the system may receive the indication of the data related to the health record of the user from the wearable device, physiological data from the wearable device, or both. The physiological data from the wearable device may be an example of temperature, heart rate, HRV, respiratory rate, sleep data, blood pressure, and the like.

In such cases, the system may adjust the sleep age metric in response to receiving the indication. For example, the sleep age metric may be adjusted based on a medical history of the patient, physiological data obtained from the wearable device, or both. The system may cause the GUI 600 to display the indication (via alert 610, sleep age card 615, and/or message 620) based on adjusting the sleep age metric. In such cases, the system may adjust the insights, recommendations, and the like based on the adjusted sleep age metric. For example, the system may indicate "It looks like you may be experiencing a cold. Your sleep age metric is higher than usual, but this will all balance out after you recover from your cold. Take some time to rest." In some examples, the system may indicate "Based on your healthy lifestyle, your sleep age metric is below your chronological age. Keep up the great work!" In other examples, the system may indicate "Your sleep age metric is equal to your chronological age. Way to go! If you would like to lower your sleep age metric, try implementing a consistent exercise routine."

As shown in FIG. 6, the application page 605 may display the indication of the sleep age metric via the sleep age card 615. In some cases, the application page 605 may display the indication of the adjusted sleep age metric via alert 610, sleep age card 615, or both. The user may receive alert 610, and the application page 605 may prompt the user to confirm or dismiss the determined sleep age metric or the adjusted sleep age metric. For example, the system may receive, via a user device and in response to adjusting the sleep age metric, a confirmation of the sleep age metric.

In some implementations, the system may provide additional insight regarding the user's determined sleep age metric. For example, the application pages 605 may indicate one or more physiological parameters (e.g., contributing factors) which resulted in the user's determined sleep age metric, such as exercise habits, sleep habits, and the like. In other words, the system may be configured to provide some information or other insights regarding the determined sleep age metric. Personalized insights may indicate aspects of collected physiological data (e.g., contributing factors within the physiological data) which were used to generate the determined sleep age metric.

In some implementations, the system may be configured to receive user inputs regarding the determined sleep age metric in order to train classifiers (e.g., supervised learning for a machine learning classifier, the first machine learning model, the second machine learning model, and the like) and improve sleep age metric determination techniques. For example, the user device may receive user inputs 625, and these user inputs 625 may then be input into the first machine learning model, second machine learning model, or both to train the machine learning model. In some cases, the PPG signal may be inputted into the machine learning model. In such cases, the system may determine the sleep age metric in response to inputting the PPG signal into the machine learning model.

In some cases, application page 605 may display one or more sleep intervals for the user, where each respective sleep interval is tagged, marked, or otherwise labeled with a classified sleep stage corresponding to each respective sleep interval. For example, the application page 605 may illustrate that a user slept for a total of 7 hours and 29 minutes. This 7 hour and 29-minute time interval is displayed as a set of sleep intervals, where each sleep interval denotes a corresponding sleep stage for the respective sleep interval.

In some cases, the respective sleep intervals may be indicated as corresponding to different sleep stages via different colors, shading, labels, patterns, and the like. The application page 605 may display total time durations for each respective sleep stage, periods of movement throughout the time interval, or both.

The application page 605 may display additional data associated with the user's sleep. For example, the application page 605 may display the user's calculated overall Sleep Score for the sleep day, individual contributors used to calculate the overall Sleep Score, and the like. The application page 605 may be configured to display at least a subset of the physiological data collected by the ring (e.g., average resting heart rate, average HRV, average temperature, and the like).

Figure 7:
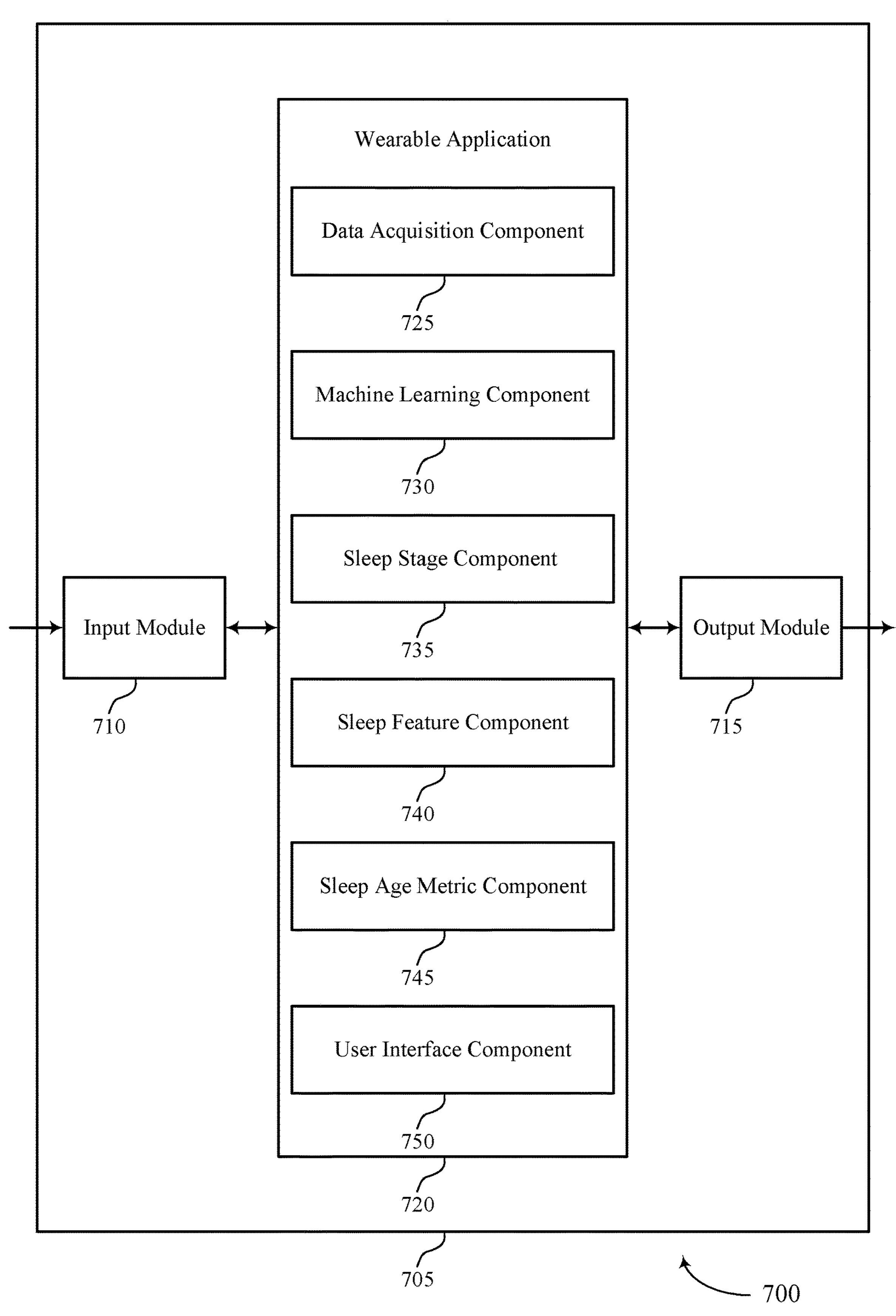
FIG. 7 shows a block diagram of an apparatus that supports sleep age determination from wearable-based physiological data in accordance with aspects of the present disclosure.

FIG. 7 shows a block diagram 700 of a device 705 that supports sleep age determination from wearable-based physiological data in accordance with aspects of the present disclosure. The device 705 may include an input module 710, an output module 715, and a wearable application 720. The device 705, or one of more components of the device 705 (e.g., the input module 710, the output module 715, and the wearable application 720), may include at least one processor, which may be coupled with at least one memory, to support the described techniques. Each of these components may be in communication with one another (e.g., via one or more buses).

The input module 710 may provide a means for receiving information such as packets, user data, control information, or any combination thereof associated with various information channels (e.g., control channels, data channels, information channels related to illness detection techniques). Information may be passed on to other components of the device 705. The input module 710 may utilize a single antenna or a set of multiple antennas.

The output module 715 may provide a means for transmitting signals generated by other components of the device 705. For example, the output module 715 may transmit information such as packets, user data, control information, or any combination thereof associated with various information channels (e.g., control channels, data channels, information channels related to illness detection techniques). In some examples, the output module 715 may be co-located with the input module 710 in a transceiver module. The output module 715 may utilize a single antenna or a set of multiple antennas.

For example, the wearable application 720 may include a data acquisition component 725, a machine learning component 730, a sleep stage component 735, a sleep feature component 740, a sleep age metric component 745, a user interface component 750, or any combination thereof. In some examples, the wearable application 720, or various components thereof, may be configured to perform various operations (e.g., receiving, monitoring, transmitting) using or otherwise in cooperation with the input module 710, the output module 715, or both. For example, the wearable application 720 may receive information from the input module 710, send information to the output module 715, or be integrated in combination with the input module 710, the output module 715, or both to receive information, transmit information, or perform various other operations as described herein.

The data acquisition component 725 may be configured as or otherwise support a means for receiving PPG data measured from the user by a wearable device throughout a time interval including a plurality of sleep intervals during which the user is asleep. The machine learning component 730 may be configured as or otherwise support a means for inputting, using one or more processors communicatively coupled with the wearable device, the PPG data into a first machine learning model. The sleep stage component 735 may be configured as or otherwise support a means for classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof. The sleep feature component 740 may be configured as or otherwise support a means for inputting one or more sleep features from the sleep staging classification procedure into a second machine learning model based at least in part on classifying the PPG data, the one or more sleep features comprising at least a duration that the user spent in each of the plurality of sleep stages. The sleep age metric component 745 may be configured as or otherwise support a means for outputting, from the second machine learning model based at least in part on inputting the one or more sleep features, a sleep age metric associated with a sleep health of the user relative to a chronological age of the user. The user interface component 750 may be configured as or otherwise support a means for transmitting, to a user device associated with the wearable device, an instruction to cause a GUI of the user device to display an indication of the sleep age metric and an insight for a value of the sleep age metric that is based at least in part on the one or more sleep features.

Figure 8:
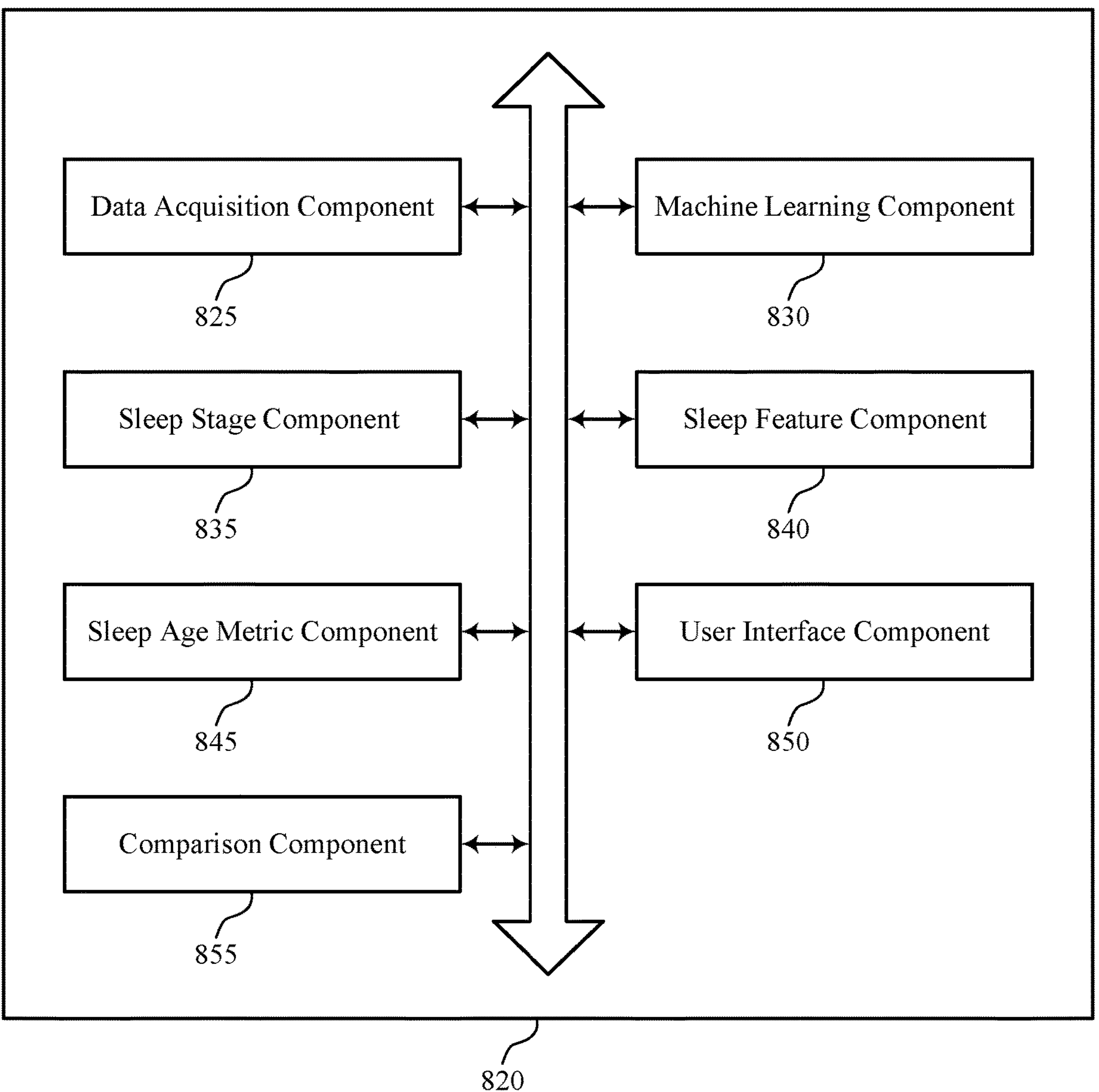
FIG. 8 shows a block diagram of a wearable application that supports sleep age determination from wearable-based physiological data in accordance with aspects of the present disclosure.

FIG. 8 shows a block diagram 800 of a wearable application 820 that supports sleep age determination from wearable-based physiological data in accordance with aspects of the present disclosure. The wearable application 820 may be an example of aspects of a wearable application or a wearable application 720, or both, as described herein. The wearable application 820, or various components thereof, may be an example of means for performing various aspects of sleep age determination from wearable-based physiological data as described herein. For example, the wearable application 820 may include a data acquisition component 825, a machine learning component 830, a sleep stage component 835, a sleep feature component 840, a sleep age metric component 845, a user interface component 850, a comparison component 855, or any combination thereof. Each of these components, or components of subcomponents thereof (e.g., one or more processors, one or more memories), may communicate, directly or indirectly, with one another (e.g., via one or more buses).

The data acquisition component 825 may be configured as or otherwise support a means for receiving PPG data measured from the user by a wearable device throughout a time interval including a plurality of sleep intervals during which the user is asleep. The machine learning component 830 may be configured as or otherwise support a means for inputting, using one or more processors communicatively coupled with the wearable device, the PPG data into a first machine learning model. The sleep stage component 835 may be configured as or otherwise support a means for classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof. The sleep feature component 840 may be configured as or otherwise support a means for inputting one or more sleep features from the sleep staging classification procedure into a second machine learning model based at least in part on classifying the PPG data, the one or more sleep features comprising at least a duration that the user spent in each of the plurality of sleep stages. The sleep age metric component 845 may be configured as or otherwise support a means for outputting, from the second machine learning model based at least in part on inputting the one or more sleep features, a sleep age metric associated with a sleep health of the user relative to a chronological age of the user. The user interface component 850 may be configured as or otherwise support a means for transmitting, to a user device associated with the wearable device, an instruction to cause a GUI of the user device to display an indication of the sleep age metric and an insight for a value of the sleep age metric that is based at least in part on the one or more sleep features.

In some examples, the sleep feature component 840 may be configured as or otherwise support a means for comparing the one or more sleep features from the sleep staging classification procedure with one or more baseline sleep features associated with the chronological age of the user based at least in part on inputting the one or more sleep features from the sleep staging classification procedure into the second machine learning model, wherein outputting the sleep age metric is based at least in part on comparing the one or more sleep features with the one or more baseline sleep features.

In some examples, the data acquisition component 825 may be configured as or otherwise support a means for receiving baseline physiological data measured from the user via the wearable device throughout a reference window that precedes the time interval. In some examples, the comparison component 855 may be configured as or otherwise support a means for identifying, based at least in part on the baseline physiological data, one or more actions engaged in by the user during the reference window, one or more environmental conditions associated with an environment of the user during the reference window, or both. In some examples, the comparison component 855 may be configured as or otherwise support a means for determining one or more relationships between the one or more sleep features and the one or more actions, the one or more environmental conditions, or both, wherein the insight is based at least in part on the one or more relationships.

In some examples, the one or more relationships comprise a relationship between the one or more actions, the one or more environmental conditions, or both, and a change in the duration that the user spent in one or more of the plurality of sleep stages during the reference window.

In some examples, the machine learning component 830 may be configured as or otherwise support a means for inputting the PPG data into the second machine learning model along with the one or more sleep features, wherein outputting the sleep age metric is based at least in part on inputting both the PPG data and the one or more sleep features into the second machine learning model.

In some examples, the data acquisition component 825 may be configured as or otherwise support a means for receiving temperature data measured from the user by the wearable device throughout the time interval including the plurality of sleep intervals during which the user is asleep. In some examples, the machine learning component 830 may be configured as or otherwise support a means for inputting the temperature data into the second machine learning model based at least in part on receiving the temperature data, wherein outputting the sleep age metric is based at least in part on inputting the temperature data into the second machine learning model.

In some examples, the data acquisition component 825 may be configured as or otherwise support a means for receiving heart rate data measured from the user by the wearable device throughout the time interval including the plurality of sleep intervals during which the user is asleep. In some examples, the machine learning component 830 may be configured as or otherwise support a means for inputting the heart rate data into the second machine learning model based at least in part on receiving the heart rate data, wherein outputting the sleep age metric is based at least in part on inputting the heart rate data into the second machine learning model.

In some examples, the comparison component 855 may be configured as or otherwise support a means for comparing the heart rate data from the plurality of sleep stages with baseline heart rate data that the user is awake based at least in part on inputting the heart rate data into the second machine learning model, wherein outputting the sleep age metric is based at least in part on comparing the heart rate data with the baseline heart rate data.

In some examples, the data acquisition component 825 may be configured as or otherwise support a means for receiving heart rate variability data measured from the user by the wearable device throughout the time interval including the plurality of sleep intervals during which the user is asleep. In some examples, the machine learning component 830 may be configured as or otherwise support a means for inputting the heart rate variability data into the second machine learning model based at least in part on receiving the heart rate variability data, wherein outputting the sleep age metric is based at least in part on inputting the heart rate variability data into the second machine learning model.

In some examples, the comparison component 855 may be configured as or otherwise support a means for comparing the heart rate variability data from the plurality of sleep stages with baseline heart rate variability data that the user is awake based at least in part on inputting the heart rate variability data into the second machine learning model, wherein outputting the sleep age metric is based at least in part on comparing the heart rate variability data with the baseline heart rate variability data.

In some examples, the data acquisition component 825 may be configured as or otherwise support a means for receiving, via the user device, a user input comprising information associated with a health record of the user. In some examples, the sleep age metric component 845 may be configured as or otherwise support a means for adjusting the sleep age metric based at least in part on receiving the user input, wherein outputting the sleep age metric is based at least in part on adjusting the sleep age metric.

In some examples, the one or more sleep features further comprise a percentage of time that the user spent in each of the plurality of sleep stages, a sleep efficiency, a quantity of times that the user transitioned between the plurality of sleep stages, a quantity of times that the user woke up during the plurality of sleep intervals, a sleep midpoint of the plurality of sleep intervals, a bed time that the user went to sleep for the plurality of sleep intervals, an awake time that the user woke up from the plurality of sleep intervals, a total time that the user spent sleeping during the plurality of sleep intervals, or a combination thereof.

In some examples, instruction is configured to cause the GUI to display a rationale for the value of the sleep age metric, recommendations to improve the sleep age metric, trends associated with the sleep age metric, educational content associated with the sleep age metric, an adjusted set of activity targets, an adjusted set of sleep targets, or a combination thereof.

In some examples, the insight for the value of the sleep age metric comprises one or more explanations for a difference between the sleep age metric and the chronological age of the user. In some examples, the one or more explanations are associated with the one or more sleep features.

In some examples, the wearable device comprises a wearable ring device.

Figure 9:
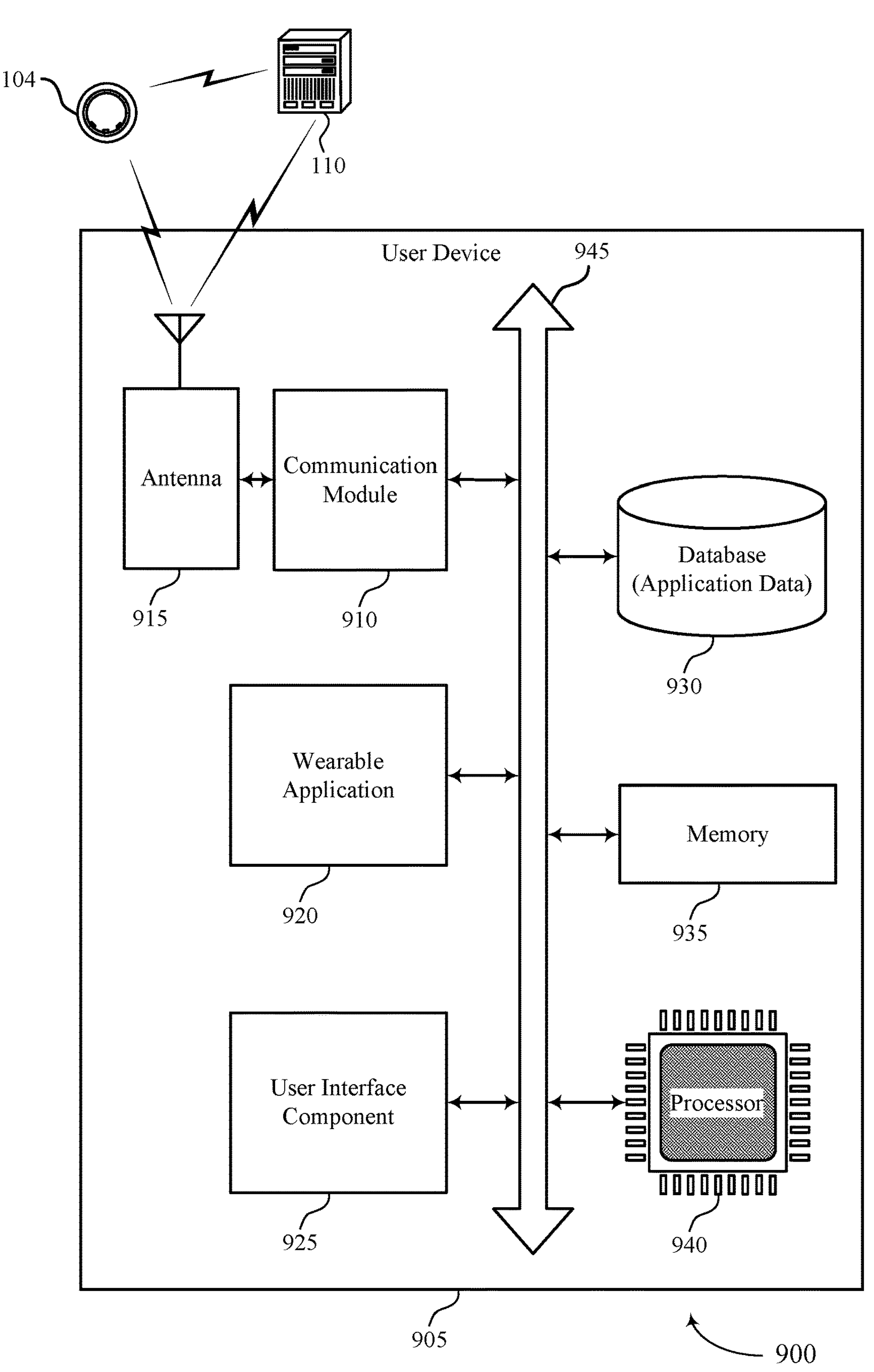
FIG. 9 shows a diagram of a system including a device that supports sleep age determination from wearable-based physiological data in accordance with aspects of the present disclosure.

FIG. 9 shows a diagram of a system 900 including a device 905 that supports sleep age determination from wearable-based physiological data in accordance with aspects of the present disclosure. The device 905 may be an example of or include the components of a device 705 as described herein. The device 905 may include an example of a user device 106, as described previously herein. The device 905 may include components for bi-directional communications including components for transmitting and receiving communications with a wearable device 104 and a server 110, such as a wearable application 920, a communication module 910, an antenna 915, a user interface component 925, a database (application data) 930, at least one memory 935, and at least one processor 940. These components may be in electronic communication or otherwise coupled (e.g., operatively, communicatively, functionally, electronically, electrically) via one or more buses (e.g., a bus 945).

The communication module 910 may manage input and output signals for the device 905 via the antenna 915. The communication module 910 may include an example of the communication module 220-*b* of the user device 106 shown and described in FIG. 2. In this regard, the communication module 910 may manage communications with the ring 104 and the server 110, as illustrated in FIG. 2. The communication module 910 may also manage peripherals not integrated into the device 905. In some cases, the communication module 910 may represent a physical connection or port to an external peripheral. In some cases, the communication module 910 may utilize an operating system such as iOS®, ANDROID®, MS-DOS®, MS-WINDOWS®, OS/2®, UNIX®, LINUX®, or another known operating system. In other cases, the communication module 910 may represent or interact with a wearable device (e.g., ring 104), modem, a keyboard, a mouse, a touchscreen, or a similar device. In some cases, the communication module 910 may be implemented as part of the processor 940. In some examples, a user may interact with the device 905 via the communication module 910, user interface component 925, or via hardware components controlled by the communication module 910.

In some cases, the device 905 may include a single antenna 915. However, in some other cases, the device 905 may have more than one antenna 915, which may be capable of concurrently transmitting or receiving multiple wireless transmissions. The communication module 910 may communicate bi-directionally, via the one or more antennas 915, wired, or wireless links as described herein. For example, the communication module 910 may represent a wireless transceiver and may communicate bi-directionally with another wireless transceiver. The communication module 910 may also include a modem to modulate the packets, to provide the modulated packets to one or more antennas 915 for transmission, and to demodulate packets received from the one or more antennas 915.

The user interface component 925 may manage data storage and processing in a database 930. In some cases, a user may interact with the user interface component 925. In other cases, the user interface component 925 may operate automatically without user interaction. The database 930 may be an example of a single database, a distributed database, multiple distributed databases, a data store, a data lake, or an emergency backup database.

The memory 935 may include RAM and ROM. The memory 935 may store computer-readable, computer-executable software including instructions that, when executed, cause the processor 940 to perform various functions described herein. In some cases, the memory 935 may contain, among other things, a BIOS which may control basic hardware or software operation such as the interaction with peripheral components or devices.

The processor 940 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 940 may be configured to operate a memory array using a memory controller. In other cases, a memory controller may be integrated into the processor 940. The processor 940 may be configured to execute computer-readable instructions stored in a memory 935 to perform various functions (e.g., functions or tasks supporting a method and system for sleep staging algorithms).

For example, the wearable application 920 may be configured as or otherwise support a means for receiving PPG data measured from the user by a wearable device throughout a time interval including a plurality of sleep intervals during which the user is asleep. The wearable application 920 may be configured as or otherwise support a means for inputting, using one or more processors communicatively coupled with the wearable device, the PPG data into a first machine learning model. The wearable application 920 may be configured as or otherwise support a means for classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof. The wearable application 920 may be configured as or otherwise support a means for inputting one or more sleep features from the sleep staging classification procedure into a second machine learning model based at least in part on classifying the PPG data, the one or more sleep features comprising at least a duration that the user spent in each of the plurality of sleep stages. The wearable application 920 may be configured as or otherwise support a means for outputting, from the second machine learning model basing at least in part on inputting the one or more sleep features, a sleep age metric associated with a sleep health of the user relative to a chronological age of the user. The wearable application 920 may be configured as or otherwise support a means for transmitting, to a user device associated with the wearable device, an instruction to cause a GUI of the user device to display an indication of the sleep age metric and an insight for a value of the sleep age metric that is based at least in part on the one or more sleep features.

By including or configuring the wearable application 920 in accordance with examples as described herein, the device 905 may support techniques for improved communication reliability, reduced latency, improved user experience related to reduced processing, reduced power consumption, more efficient utilization of communication resources, improved coordination between devices, longer battery life, improved utilization of processing capability, and the like.

The wearable application 920 may include an application (e.g., "app"), program, software, or other component which is configured to facilitate communications with a ring 104, server 110, other user devices 106, and the like. For example, the wearable application 920 may include an application executable on a user device 106 which is configured to receive data (e.g., physiological data) from a ring 104, perform processing operations on the received data, transmit and receive data with the servers 110, and cause presentation of data to a user 102.

Figure 10:
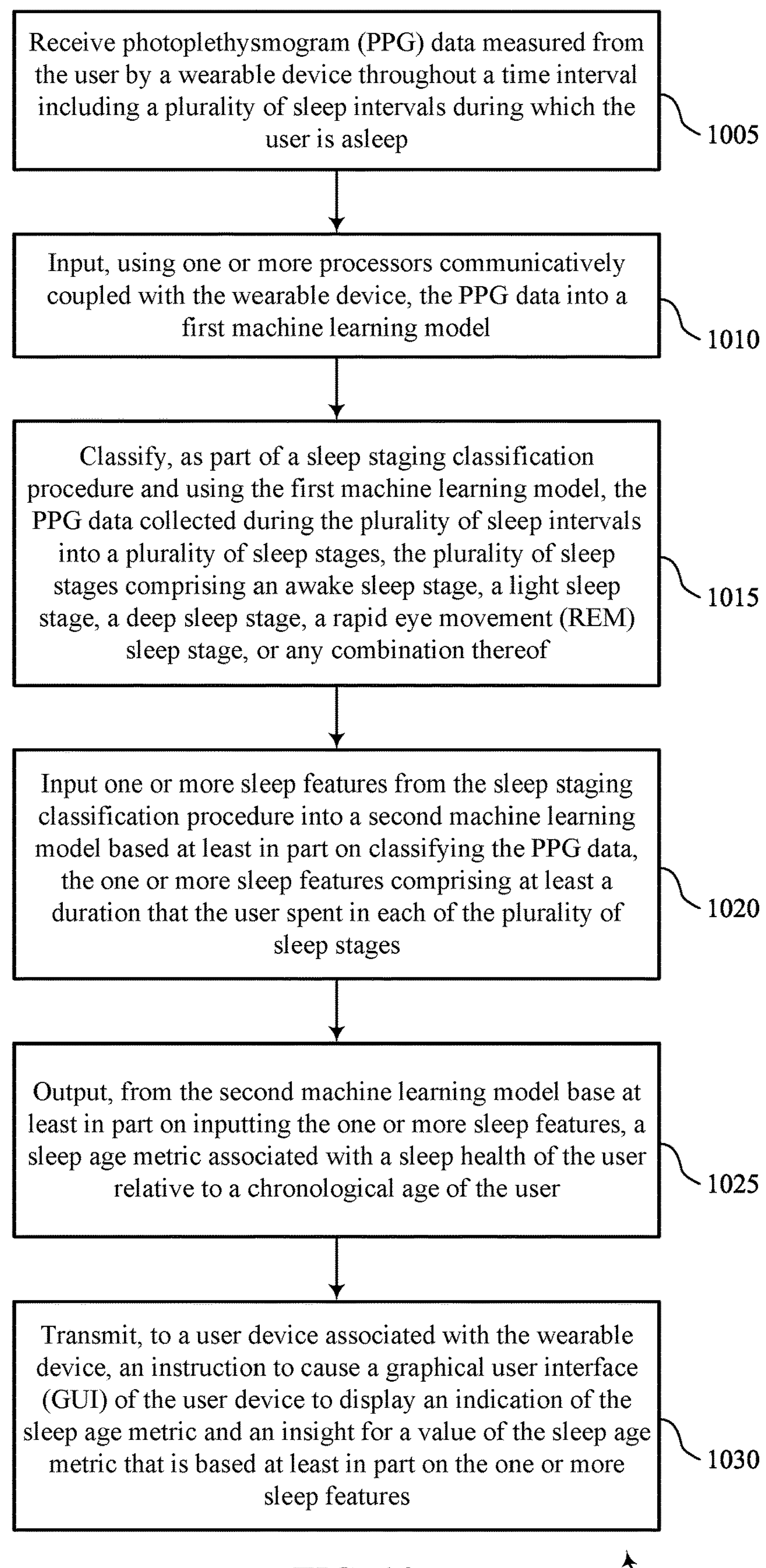
FIGS. 10 through 12 show flowcharts illustrating methods that support sleep age determination from wearable-based physiological data in accordance with aspects of the present disclosure.

FIG. 10 shows a flowchart illustrating a method 1000 that supports sleep age determination from wearable-based physiological data in accordance with aspects of the present disclosure. The operations of the method 1000 may be implemented by a user device or its components as described herein. For example, the operations of the method 1000 may be performed by a user device as described with reference to FIGS. 1 through 9. In some examples, a user device may execute a set of instructions to control the functional elements of the user device to perform the described functions. Additionally, or alternatively, the user device may perform aspects of the described functions using special-purpose hardware.

At 1005, the method may include receiving PPG data measured from the user by a wearable device throughout a time interval including a plurality of sleep intervals during which the user is asleep. The operations of block 1005 may be performed in accordance with examples as disclosed herein. In some examples, aspects of the operations of 1005 may be performed by a data acquisition component 825 as described with reference to FIG. 8.

At 1010, the method may include inputting, using one or more processors communicatively coupled with the wearable device, the PPG data into a first machine learning model. The operations of block 1010 may be performed in accordance with examples as disclosed herein. In some examples, aspects of the operations of 1010 may be performed by a machine learning component 830 as described with reference to FIG. 8.

At 1015, the method may include classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof. The operations of block 1015 may be performed in accordance with examples as disclosed herein. In some examples, aspects of the operations of 1015 may be performed by a sleep stage component 835 as described with reference to FIG. 8.

At 1020, the method may include inputting one or more sleep features from the sleep staging classification procedure into a second machine learning model based at least in part on classifying the PPG data, the one or more sleep features comprising at least a duration that the user spent in each of the plurality of sleep stages. The operations of block 1020 may be performed in accordance with examples as disclosed herein. In some examples, aspects of the operations of 1020 may be performed by a sleep feature component 840 as described with reference to FIG. 8.

At 1025, the method may include outputting, from the second machine learning model based at least in part on inputting the one or more sleep features, a sleep age metric associated with a sleep health of the user relative to a chronological age of the user. The operations of block 1025 may be performed in accordance with examples as disclosed herein. In some examples, aspects of the operations of 1025 may be performed by a sleep age metric component 845 as described with reference to FIG. 8.

At 1030, the method may include transmitting, to a user device associated with the wearable device, an instruction to cause a GUI of the user device to display an indication of the sleep age metric and an insight for a value of the sleep age metric that is based at least in part on the one or more sleep features. The operations of block 1030 may be performed in accordance with examples as disclosed herein. In some examples, aspects of the operations of 1030 may be performed by a user interface component 850 as described with reference to FIG. 8.

Figure 11:
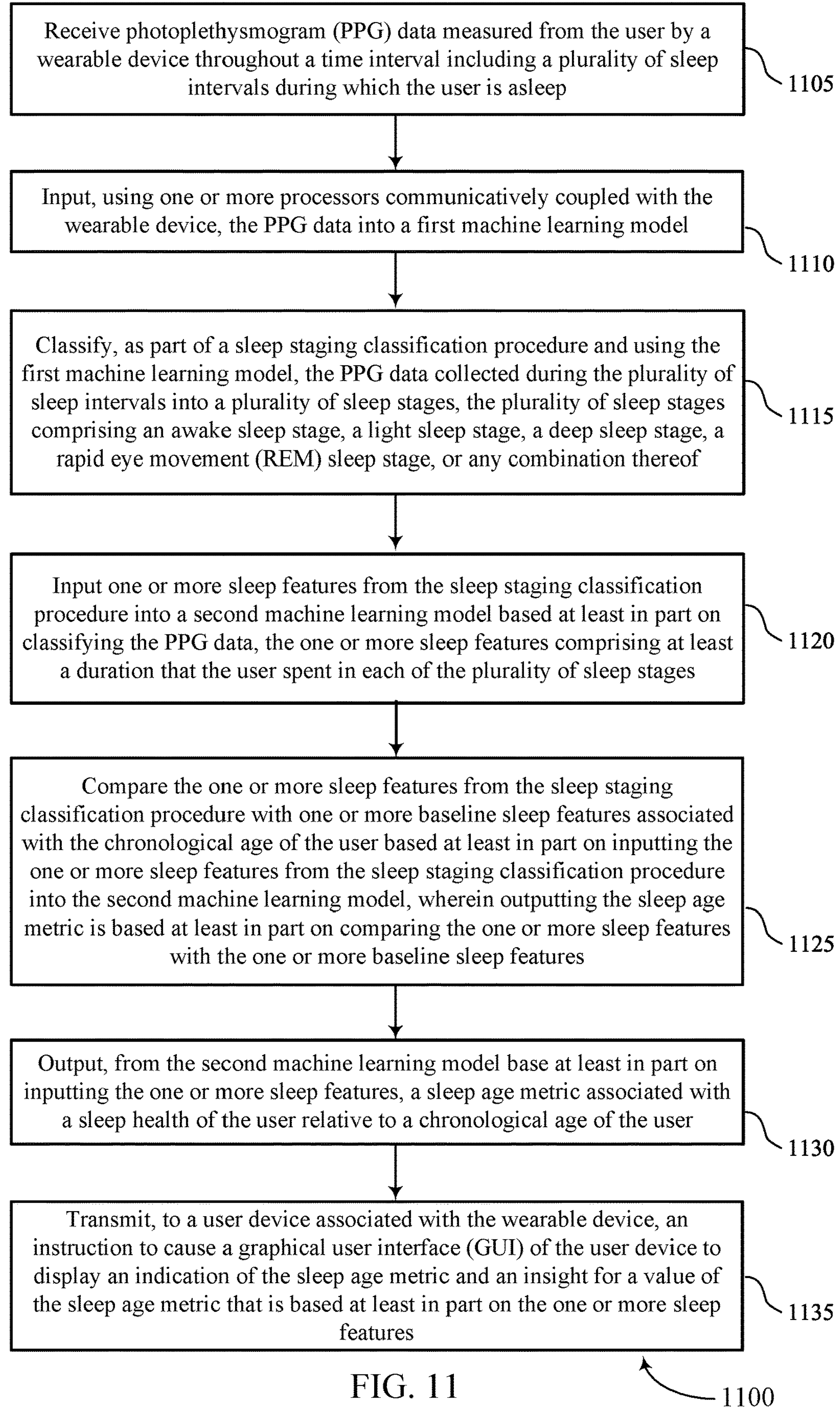

FIG. 11 shows a flowchart illustrating a method 1100 that supports sleep age determination from wearable-based physiological data in accordance with aspects of the present disclosure. The operations of the method 1100 may be implemented by a user device or its components as described herein. For example, the operations of the method 1100 may be performed by a user device as described with reference to FIGS. 1 through 9. In some examples, a user device may execute a set of instructions to control the functional elements of the user device to perform the described functions. Additionally, or alternatively, the user device may perform aspects of the described functions using special-purpose hardware.

At 1105, the method may include receiving PPG data measured from the user by a wearable device throughout a time interval including a plurality of sleep intervals during which the user is asleep. The operations of block 1105 may be performed in accordance with examples as disclosed herein. In some examples, aspects of the operations of 1105 may be performed by a data acquisition component 825 as described with reference to FIG. 8.

At 1110, the method may include inputting, using one or more processors communicatively coupled with the wearable device, the PPG data into a first machine learning model. The operations of block 1110 may be performed in accordance with examples as disclosed herein. In some examples, aspects of the operations of 1110 may be performed by a machine learning component 830 as described with reference to FIG. 8.

At 1115, the method may include classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof. The operations of block 1115 may be performed in accordance with examples as disclosed herein. In some examples, aspects of the operations of 1115 may be performed by a sleep stage component 835 as described with reference to FIG. 8.

At 1120, the method may include inputting one or more sleep features from the sleep staging classification procedure into a second machine learning model based at least in part on classifying the PPG data, the one or more sleep features comprising at least a duration that the user spent in each of the plurality of sleep stages. The operations of block 1120 may be performed in accordance with examples as disclosed herein. In some examples, aspects of the operations of 1120 may be performed by a sleep feature component 840 as described with reference to FIG. 8.

At 1125, the method may include comparing the one or more sleep features from the sleep staging classification procedure with one or more baseline sleep features associated with the chronological age of the user based at least in part on inputting the one or more sleep features from the sleep staging classification procedure into the second machine learning model, wherein outputting the sleep age metric is based at least in part on comparing the one or more sleep features with the one or more baseline sleep features. The operations of block 1135 may be performed in accordance with examples as disclosed herein. In some examples, aspects of the operations of 1135 may be performed by a sleep feature component 840 as described with reference to FIG. 8.

At 1130, the method may include outputting, from the second machine learning model based at least in part on inputting the one or more sleep features, a sleep age metric associated with a sleep health of the user relative to a chronological age of the user. The operations of block 1125 may be performed in accordance with examples as disclosed herein. In some examples, aspects of the operations of 1125 may be performed by a sleep age metric component 845 as described with reference to FIG. 8.

At 1135, the method may include transmitting, to a user device associated with the wearable device, an instruction to cause a GUI of the user device to display an indication of the sleep age metric and an insight for a value of the sleep age metric that is based at least in part on the one or more sleep features. The operations of block 1130 may be performed in accordance with examples as disclosed herein. In some examples, aspects of the operations of 1130 may be performed by a user interface component 850 as described with reference to FIG. 8.

Figure 12:
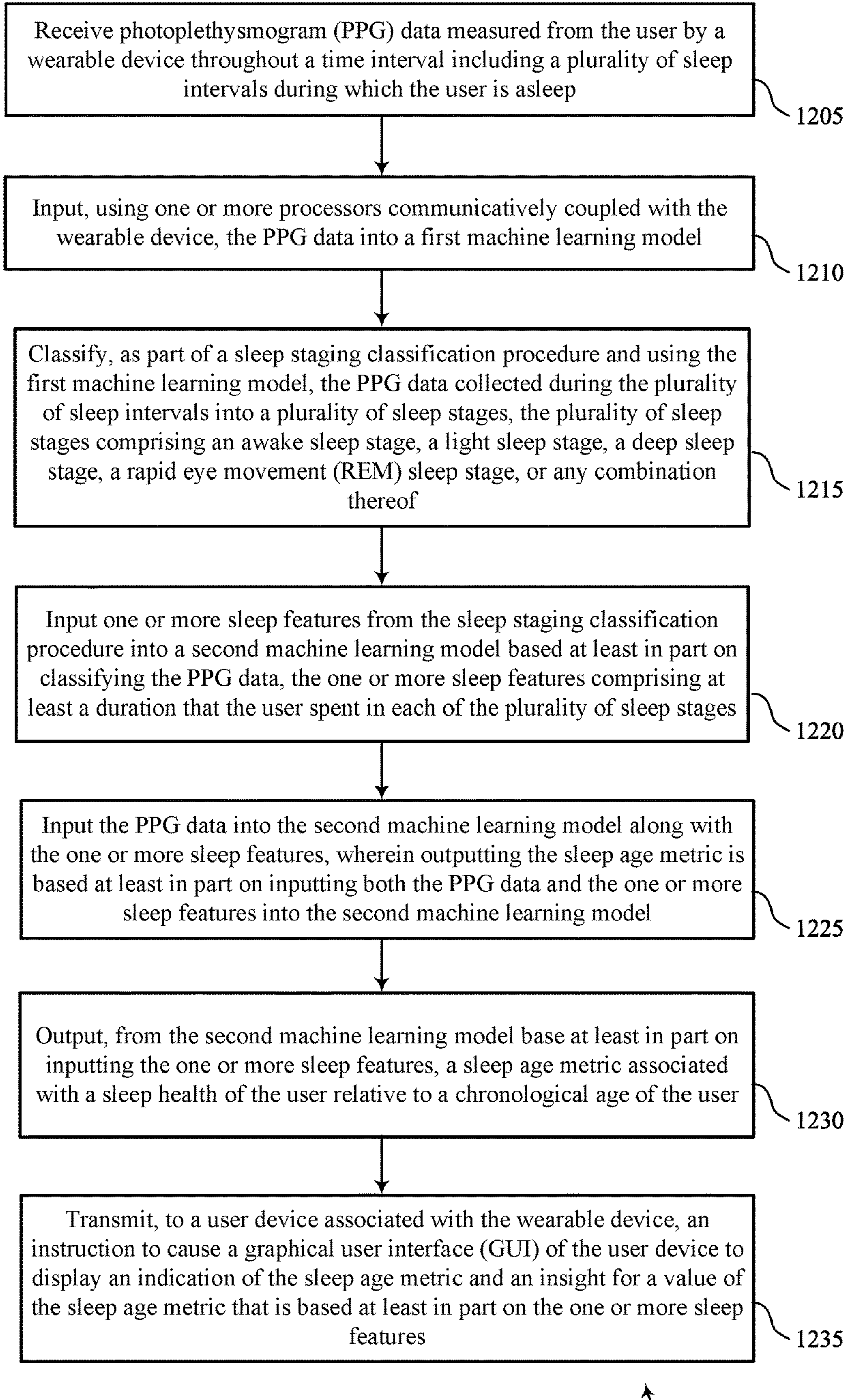

FIG. 12 shows a flowchart illustrating a method 1200 that supports sleep age determination from wearable-based physiological data in accordance with aspects of the present disclosure. The operations of the method 1200 may be implemented by a user device or its components as described herein. For example, the operations of the method 1200 may be performed by a user device as described with reference to FIGS. 1 through 9. In some examples, a user device may execute a set of instructions to control the functional elements of the user device to perform the described functions. Additionally, or alternatively, the user device may perform aspects of the described functions using special-purpose hardware.

At 1205, the method may include receiving PPG data measured from the user by a wearable device throughout a time interval including a plurality of sleep intervals during which the user is asleep. The operations of block 1205 may be performed in accordance with examples as disclosed herein. In some examples, aspects of the operations of 1205 may be performed by a data acquisition component 825 as described with reference to FIG. 8.

At 1210, the method may include inputting, using one or more processors communicatively coupled with the wearable device, the PPG data into a first machine learning model. The operations of block 1210 may be performed in accordance with examples as disclosed herein. In some examples, aspects of the operations of 1210 may be performed by a machine learning component 830 as described with reference to FIG. 8.

At 1215, the method may include classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a rapid eye movement (REM) sleep stage, or any combination thereof. The operations of block 1215 may be performed in accordance with examples as disclosed herein. In some examples, aspects of the operations of 1215 may be performed by a sleep stage component 835 as described with reference to FIG. 8.

At 1220, the method may include inputting one or more sleep features from the sleep staging classification procedure into a second machine learning model based at least in part on classifying the PPG data, the one or more sleep features comprising at least a duration that the user spent in each of the plurality of sleep stages. The operations of block 1220 may be performed in accordance with examples as disclosed herein. In some examples, aspects of the operations of 1220 may be performed by a sleep feature component 840 as described with reference to FIG. 8.

At 1225, the method may include inputting the PPG data into the second machine learning model along with the one or more sleep features, wherein outputting the sleep age metric is based at least in part on inputting both the PPG data and the one or more sleep features into the second machine learning model. The operations of block 1235 may be performed in accordance with examples as disclosed herein. In some examples, aspects of the operations of 1235 may be performed by a machine learning component 830 as described with reference to FIG. 8.

At 1230, the method may include outputting, from the second machine learning model based at least in part on inputting the one or more sleep features, a sleep age metric associated with a sleep health of the user relative to a chronological age of the user. The operations of block 1225 may be performed in accordance with examples as disclosed herein. In some examples, aspects of the operations of 1225 may be performed by a sleep age metric component 845 as described with reference to FIG. 8.

At 1235, the method may include transmitting, to a user device associated with the wearable device, an instruction to cause a GUI of the user device to display an indication of the sleep age metric and an insight for a value of the sleep age metric that is based at least in part on the one or more sleep features. The operations of block 1230 may be performed in accordance with examples as disclosed herein. In some examples, aspects of the operations of 1230 may be performed by a user interface component 850 as described with reference to FIG. 8.

It should be noted that the methods described above describe possible implementations, and that the operations and the steps may be rearranged or otherwise modified and that other implementations are possible. Furthermore, aspects from two or more of the methods may be combined.

A method by an apparatus is described. The method may include receiving PPG data measured from the user by a wearable device throughout a time interval including a plurality of sleep intervals during which the user is asleep, inputting, using one or more processors communicatively coupled with the wearable device, the PPG data into a first machine learning model, classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof, inputting one or more sleep features from the sleep staging classification procedure into a second machine learning model based at least in part on classifying the PPG data, the one or more sleep features comprising at least a duration that the user spent in each of the plurality of sleep stages, outputting, from the second machine learning model based at least in part on inputting the one or more sleep features, a sleep age metric associated with a sleep health of the user relative to a chronological age of the user, and transmitting, to a user device associated with the wearable device, an instruction to cause a GUI of the user device to display an indication of the sleep age metric and an insight for a value of the sleep age metric that is based at least in part on the one or more sleep features.

An apparatus is described. The apparatus may include one or more memories storing processor executable code, and one or more processors coupled with the one or more memories. The one or more processors may individually or collectively operable to execute the code to cause the apparatus to receive PPG data measured from the user by a wearable device throughout a time interval including a plurality of sleep intervals during which the user is asleep, input, using one or more processors communicatively coupled with the wearable device, the PPG data into a first machine learning model, classify, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof, input one or more sleep features from the sleep staging classification procedure into a second machine learning model based at least in part on classifying the PPG data, the one or more sleep features comprising at least a duration that the user spent in each of the plurality of sleep stages, outputting, from the second machine learning model base at least in part on inputting the one or more sleep features, a sleep age metric associated with a sleep health of the user relative to a chronological age of the user, and transmit, to a user device associated with the wearable device, an instruction to cause a GUI of the user device to display an indication of the sleep age metric and an insight for a value of the sleep age metric that is based at least in part on the one or more sleep features.

Another apparatus is described. The apparatus may include means for receiving PPG data measured from the user by a wearable device throughout a time interval including a plurality of sleep intervals during which the user is asleep, means for inputting, using one or more processors communicatively coupled with the wearable device, the PPG data into a first machine learning model, means for classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof, means for inputting one or more sleep features from the sleep staging classification procedure into a second machine learning model based at least in part on classifying the PPG data, the one or more sleep features comprising at least a duration that the user spent in each of the plurality of sleep stages, means for outputting, from the second machine learning model based at least in part on inputting the one or more sleep features, a sleep age metric associated with a sleep health of the user relative to a chronological age of the user, and means for transmitting, to a user device associated with the wearable device, an instruction to cause a GUI of the user device to display an indication of the sleep age metric and an insight for a value of the sleep age metric that is based at least in part on the one or more sleep features.

A non-transitory computer-readable medium storing code is described. The code may include instructions executable by a processor to receive PPG data measured from the user by a wearable device throughout a time interval including a plurality of sleep intervals during which the user is asleep, input, using one or more processors communicatively coupled with the wearable device, the PPG data into a first machine learning model, classify, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a REM sleep stage, or any combination thereof, input one or more sleep features from the sleep staging classification procedure into a second machine learning model based at least in part on classifying the PPG data, the one or more sleep features comprising at least a duration that the user spent in each of the plurality of sleep stages, outputting, from the second machine learning model base at least in part on inputting the one or more sleep features, a sleep age metric associated with a sleep health of the user relative to a chronological age of the user, and transmit, to a user device associated with the wearable device, an instruction to cause a GUI of the user device to display an indication of the sleep age metric and an insight for a value of the sleep age metric that is based at least in part on the one or more sleep features.

Some examples of the method, apparatus, and non-transitory computer-readable medium described herein may further include operations, features, means, or instructions for comparing the one or more sleep features from the sleep staging classification procedure with one or more baseline sleep features associated with the chronological age of the user based at least in part on inputting the one or more sleep features from the sleep staging classification procedure into the second machine learning model, wherein outputting the sleep age metric may be based at least in part on comparing the one or more sleep features with the one or more baseline sleep features.

Some examples of the method, apparatus, and non-transitory computer-readable medium described herein may further include operations, features, means, or instructions for receiving baseline physiological data measured from the user via the wearable device throughout a reference window that precedes the time interval, identifying, based at least in part on the baseline physiological data, one or more actions engaged in by the user during the reference window, one or more environmental conditions associated with an environment of the user during the reference window, or both, and determining one or more relationships between the one or more sleep features and the one or more actions, the one or more environmental conditions, or both, wherein the insight may be based at least in part on the one or more relationships.

In some examples of the method, apparatus, and non-transitory computer-readable medium described herein, the one or more relationships comprise a relationship between the one or more actions, the one or more environmental conditions, or both, and a change in the duration that the user spent in one or more of the plurality of sleep stages during the reference window.

Some examples of the method, apparatus, and non-transitory computer-readable medium described herein may further include operations, features, means, or instructions for inputting the PPG data into the second machine learning model along with the one or more sleep features, wherein outputting the sleep age metric may be based at least in part on inputting both the PPG data and the one or more sleep features into the second machine learning model.

Some examples of the method, apparatus, and non-transitory computer-readable medium described herein may further include operations, features, means, or instructions for receiving temperature data measured from the user by the wearable device throughout the time interval including the plurality of sleep intervals during which the user may be asleep and inputting the temperature data into the second machine learning model based at least in part on receiving the temperature data, wherein outputting the sleep age metric may be based at least in part on inputting the temperature data into the second machine learning model.

Some examples of the method, apparatus, and non-transitory computer-readable medium described herein may further include operations, features, means, or instructions for receiving heart rate data measured from the user by the wearable device throughout the time interval including the plurality of sleep intervals during which the user may be asleep and inputting the heart rate data into the second machine learning model based at least in part on receiving the heart rate data, wherein outputting the sleep age metric may be based at least in part on inputting the heart rate data into the second machine learning model.

Some examples of the method, apparatus, and non-transitory computer-readable medium described herein may further include operations, features, means, or instructions for comparing the heart rate data from the plurality of sleep stages with baseline heart rate data that the user may be awake based at least in part on inputting the heart rate data into the second machine learning model, wherein outputting the sleep age metric may be based at least in part on comparing the heart rate data with the baseline heart rate data.

Some examples of the method, apparatus, and non-transitory computer-readable medium described herein may further include operations, features, means, or instructions for receiving heart rate variability data measured from the user by the wearable device throughout the time interval including the plurality of sleep intervals during which the user may be asleep and inputting the heart rate variability data into the second machine learning model based at least in part on receiving the heart rate variability data, wherein outputting the sleep age metric may be based at least in part on inputting the heart rate variability data into the second machine learning model.

Some examples of the method, apparatus, and non-transitory computer-readable medium described herein may further include operations, features, means, or instructions for comparing the heart rate variability data from the plurality of sleep stages with baseline heart rate variability data that the user may be awake based at least in part on inputting the heart rate variability data into the second machine learning model, wherein outputting the sleep age metric may be based at least in part on comparing the heart rate variability data with the baseline heart rate variability data.

Some examples of the method, apparatus, and non-transitory computer-readable medium described herein may further include operations, features, means, or instructions for receiving, via the user device, a user input comprising information associated with a health record of the user and adjusting the sleep age metric based at least in part on receiving the user input, wherein outputting the sleep age metric may be based at least in part on adjusting the sleep age metric.

In some examples of the method, apparatus, and non-transitory computer-readable medium described herein, the one or more sleep features further comprise a percentage of time that the user spent in each of the plurality of sleep stages, a sleep efficiency, a quantity of times that the user transitioned between the plurality of sleep stages, a quantity of times that the user woke up during the plurality of sleep intervals, a sleep midpoint of the plurality of sleep intervals, a bed time that the user went to sleep for the plurality of sleep intervals, an awake time that the user woke up from the plurality of sleep intervals, a total time that the user spent sleeping during the plurality of sleep intervals, or a combination thereof.

In some examples of the method, apparatus, and non-transitory computer-readable medium described herein, instruction may be configured to cause the GUI to display a rationale for the value of the sleep age metric, recommendations to improve the sleep age metric, trends associated with the sleep age metric, educational content associated with the sleep age metric, an adjusted set of activity targets, an adjusted set of sleep targets, or a combination thereof.

In some examples of the method, apparatus, and non-transitory computer-readable medium described herein, the insight for the value of the sleep age metric comprises one or more explanations for a difference between the sleep age metric and the chronological age of the user and the one or more explanations may be associated with the one or more sleep features.

In some examples of the method, apparatus, and non-transitory computer-readable medium described herein, the wearable device comprises a wearable ring device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for determining a sleep age metric of a user comprising:

acquiring, via one or more sensors of a wearable ring device configured to be worn on a finger of a user, photoplethysmogram (PPG) data throughout a time interval including a plurality of sleep intervals during which the user is asleep;

inputting, using one or more processors communicatively coupled with the wearable ring device, the PPG data into a first machine learning model;

classifying, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a rapid eye movement (REM) sleep stage, or any combination thereof;

inputting one or more sleep features from the sleep staging classification procedure into a second machine learning model based at least in part on classifying the PPG data, the one or more sleep features comprising at least a duration that the user spent in each of the plurality of sleep stages;

outputting, from the second machine learning model based at least in part on inputting the one or more sleep features, the sleep age metric associated with a sleep health of the user relative to a chronological age of the user; and transmitting, to a user device associated with the wearable ring device, an instruction to cause a graphical user interface (GUI) of the user device to display an indication of the sleep age metric and an insight for a value of the sleep age metric that is based at least in part on the one or more sleep features.

2. The method of claim 1, further comprising:

comparing the one or more sleep features from the sleep staging classification procedure with one or more baseline sleep features associated with the chronological age of the user based at least in part on inputting the one or more sleep features from the sleep staging classification procedure into the second machine learning model, wherein outputting the sleep age metric is based at least in part on comparing the one or more sleep features with the one or more baseline sleep features.

3. The method of claim 1, further comprising:

receiving baseline physiological data measured from the user via the wearable ring device throughout a reference window that precedes the time interval;

identifying, based at least in part on the baseline physiological data, one or more actions engaged in by the user during the reference window, one or more environmental conditions associated with an environment of the user during the reference window, or both; and determining one or more relationships between the one or more sleep features and the one or more actions, the one or more environmental conditions, or both, wherein the insight is based at least in part on the one or more relationships.

4. The method of claim 3, wherein the one or more relationships comprise a relationship between the one or more actions, the one or more environmental conditions, or both, and a change in the duration that the user spent in one or more of the plurality of sleep stages during the reference window.

5. The method of claim 1, further comprising:
inputting the PPG data into the second machine learning model along with the one or more sleep features, wherein outputting the sleep age metric is based at least in part on inputting both the PPG data and the one or more sleep features into the second machine learning model.

6. The method of claim 1, further comprising:
receiving temperature data measured from the user by the wearable ring device throughout the time interval including the plurality of sleep intervals during which the user is asleep; and
inputting the temperature data into the second machine learning model based at least in part on receiving the temperature data, wherein outputting the sleep age metric is based at least in part on inputting the temperature data into the second machine learning model.

7. The method of claim 1, further comprising:
receiving heart rate data measured from the user by the wearable ring device throughout the time interval including the plurality of sleep intervals during which the user is asleep; and
inputting the heart rate data into the second machine learning model based at least in part on receiving the heart rate data, wherein outputting the sleep age metric is based at least in part on inputting the heart rate data into the second machine learning model.

8. The method of claim 7, further comprising:
comparing the heart rate data from the plurality of sleep stages with baseline heart rate data during which the user is awake based at least in part on inputting the heart rate data into the second machine learning model, wherein outputting the sleep age metric is based at least in part on comparing the heart rate data with the baseline heart rate data.

9. The method of claim 1, further comprising:
receiving heart rate variability data measured from the user by the wearable ring device throughout the time interval including the plurality of sleep intervals during which the user is asleep; and
inputting the heart rate variability data into the second machine learning model based at least in part on receiving the heart rate variability data, wherein outputting the sleep age metric is based at least in part on inputting the heart rate variability data into the second machine learning model.

10. The method of claim 9, further comprising:
comparing the heart rate variability data from the plurality of sleep stages with baseline heart rate variability data during which the user is awake based at least in part on inputting the heart rate variability data into the second machine learning model, wherein outputting the sleep age metric is based at least in part on comparing the heart rate variability data with the baseline heart rate variability data.

11. The method of claim 1, further comprising:
receiving, via the user device, a user input comprising information associated with a health record of the user; and
adjusting the sleep age metric based at least in part on receiving the user input, wherein outputting the sleep age metric is based at least in part on adjusting the sleep age metric.

12. The method of claim 1, wherein the one or more sleep features further comprise a percentage of time that the user spent in each of the plurality of sleep stages, a sleep efficiency, a quantity of times that the user transitioned between the plurality of sleep stages, a quantity of times that the user woke up during the plurality of sleep intervals, a sleep midpoint of the plurality of sleep intervals, a bed time at which the user went to sleep for the plurality of sleep intervals, an awake time at which the user woke up from the plurality of sleep intervals, a total time that the user spent sleeping during the plurality of sleep intervals, or a combination thereof.

13. The method of claim 1, wherein the instruction is configured to cause the GUI to display a rationale for the value of the sleep age metric, recommendations to improve the sleep age metric, trends associated with the sleep age metric, educational content associated with the sleep age metric, an adjusted set of activity targets, an adjusted set of sleep targets, or a combination thereof.

14. The method of claim 1, wherein the insight for the value of the sleep age metric comprises one or more explanations for a difference between the sleep age metric and the chronological age of the user, wherein the one or more explanations are associated with the one or more sleep features.

15. An apparatus, comprising:
one or more memories storing processor-executable code; and
one or more processors coupled with the one or more memories and individually or collectively operable to execute the code to cause the apparatus to:
acquire, via one or more sensors of a wearable ring device configured to be worn on a finger of a user, photoplethysmogram (PPG) data throughout a time interval including a plurality of sleep intervals during which the user is asleep;
input, using the one or more processors communicatively coupled with the wearable ring device, the PPG data into a first machine learning model;
classify, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a rapid eye movement (REM) sleep stage, or any combination thereof;
input one or more sleep features from the sleep staging classification procedure into a second machine learning model based at least in part on classifying the PPG data, the one or more sleep features comprising at least a duration that the user spent in each of the plurality of sleep stages;
outputting, from the second machine learning model based at least in part on inputting the one or more sleep features, a sleep age metric associated with a sleep health of the user relative to a chronological age of the user; and
transmit, to a user device associated with the wearable ring device, an instruction to cause a graphical user interface (GUI) of the user device to display an indication of the sleep age metric and an insight for a value of the sleep age metric that is based at least in part on the one or more sleep features.

16. The apparatus of claim 15, wherein the one or more processors are individually or collectively further operable to execute the code to cause the apparatus to:
compare the one or more sleep features from the sleep staging classification procedure with one or more baseline sleep features associated with the chronological age of the user based at least in part on inputting the one or more sleep features from the sleep staging classification procedure into the second machine learning model, wherein outputting the sleep age metric is based at least in part on comparing the one or more sleep features with the one or more baseline sleep features.

17. The apparatus of claim 15, wherein the one or more processors are individually or collectively further operable to execute the code to cause the apparatus to:

receive baseline physiological data measured from the user via the wearable ring device throughout a reference window that precedes the time interval;

identifying, base at least in part on the baseline physiological data, one or more actions engaged in by the user during the reference window, one or more environmental conditions associated with an environment of the user during the reference window, or both; and determine one or more relationships between the one or more sleep features and the one or more actions, the one or more environmental conditions, or both, wherein the insight is based at least in part on the one or more relationships.

18. A non-transitory computer-readable medium storing code, the code comprising instructions executable by one or more processors to:

acquire, via one or more sensors of a wearable ring device configured to be worn on a finger of a user, photoplethysmogram (PPG) data throughout a time interval including a plurality of sleep intervals during which the user is asleep;

input, using the one or more processors communicatively coupled with the wearable ring device, the PPG data into a first machine learning model;

classify, as part of a sleep staging classification procedure and using the first machine learning model, the PPG data collected during the plurality of sleep intervals into a plurality of sleep stages, the plurality of sleep stages comprising an awake sleep stage, a light sleep stage, a deep sleep stage, a rapid eye movement (REM) sleep stage, or any combination thereof;

input one or more sleep features from the sleep staging classification procedure into a second machine learning model based at least in part on classifying the PPG data, the one or more sleep features comprising at least a duration that the user spent in each of the plurality of sleep stages;

outputting, from the second machine learning model based at least in part on inputting the one or more sleep features, a sleep age metric associated with a sleep health of the user relative to a chronological age of the user; and transmit, to a user device associated with the wearable ring device, an instruction to cause a graphical user interface (GUI) of the user device to display an indication of the sleep age metric and an insight for a value of the sleep age metric that is based at least in part on the one or more sleep features.

19. The non-transitory computer-readable medium of claim 18, wherein the instructions are further executable by the one or more processors to:

compare the one or more sleep features from the sleep staging classification procedure with one or more baseline sleep features associated with the chronological age of the user based at least in part on inputting the one or more sleep features from the sleep staging classification procedure into the second machine learning model, wherein outputting the sleep age metric is based at least in part on comparing the one or more sleep features with the one or more baseline sleep features.

* * * * *